United States Patent
Von Schuckmann et al.

(10) Patent No.: US 6,520,179 B1
(45) Date of Patent: Feb. 18, 2003

(54) INHALATION DEVICE

(75) Inventors: Alfred Von Schuckmann, Kevelaer (DE); Björn Ullbrand, Löddeköpinge (SE); Anders Selmer, Skurup (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/582,180

(22) PCT Filed: Dec. 22, 1998

(86) PCT No.: PCT/EP98/08456

§ 371 (c)(1),
(2), (4) Date: Nov. 2, 2000

(87) PCT Pub. No.: WO99/31952

PCT Pub. Date: Jul. 1, 1999

(30) Foreign Application Priority Data

Dec. 22, 1997 (DE) ............................... 197 57 208
Dec. 22, 1997 (DE) ............................... 197 57 207

(51) Int. Cl.⁷ ................................................. B65D 83/06
(52) U.S. Cl. ........................... 128/203.15; 128/203.12; 128/203.21; 128/203.23
(58) Field of Search .................. 128/200.14, 200.24, 128/203.12, 202.21, 203.15, 203.21, 203.23; 604/58.64

(56) References Cited

U.S. PATENT DOCUMENTS

| 5,133,454 A | 7/1992 | Hammer |
|---|---|---|
| 5,533,502 A | 7/1996 | Piper |
| 5,595,175 A * | 1/1997 | Malcher et al. ........ 128/203.15 |
| 6,089,228 A * | 7/2000 | Smith et al. ........... 128/203.15 |

FOREIGN PATENT DOCUMENTS

| DE | 196 19 536 A1 | 10/1997 |
|---|---|---|
| EP | 0 129 985 | 1/1985 |
| WO | WO 96/07601 | 3/1996 |
| WO | WO 96/09085 | 3/1996 |
| WO | WO 97/04827 | 2/1997 |
| WO | WO 97/40876 | 11/1997 |

OTHER PUBLICATIONS

International Search Report PCT/EP 98/08456.

* cited by examiner

Primary Examiner—Glenn K. Dawson
(74) Attorney, Agent, or Firm—Fish & Richardson P.C.

(57) ABSTRACT

A blister pack assembly for an inhaler for administering powder containing medicament by inhalation, comprising: a suction tube (7) through which powder is in use drawn on inhalation by a user; and a blister pack unit (5) comprising a blister pack element (11) which includes a plurality of blisters (12), each containing a dose of powder containing medicament, and an attachment member (13) disposed to one side of the blister pack element (11) to which the suction (7) is attachable when not in use.

14 Claims, 24 Drawing Sheets

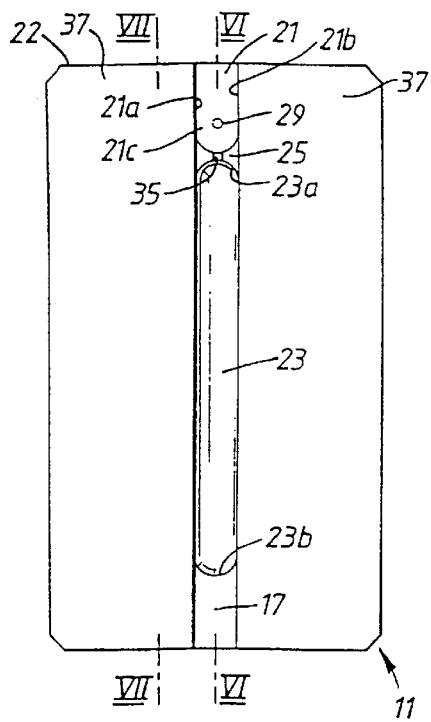
Fig.16(a)
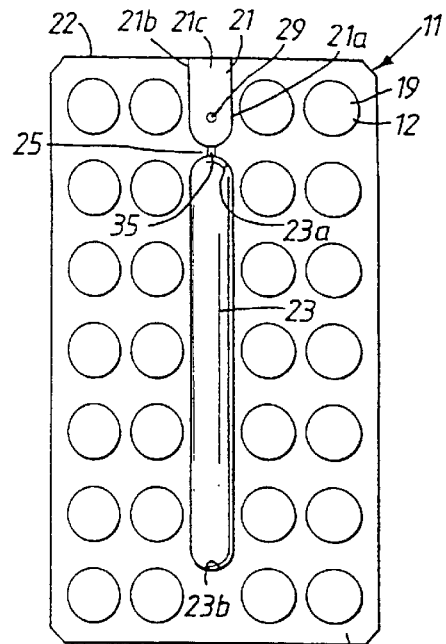
Fig.16(b)
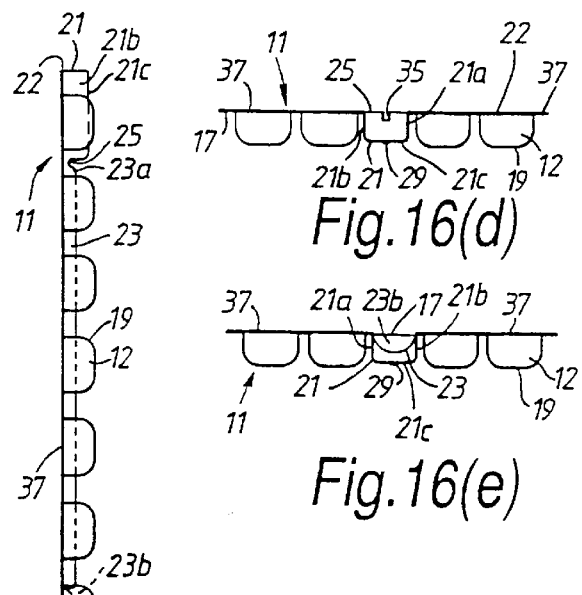
Fig.16(d)
Fig.16(e)
Fig.16(c)
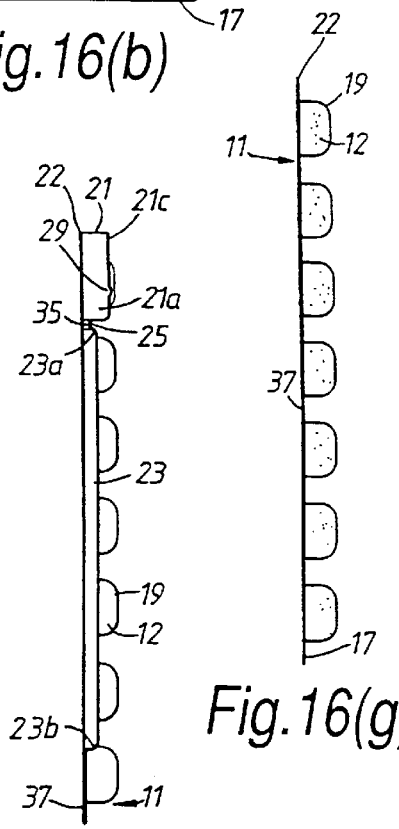
Fig.16(f)
Fig.16(g)

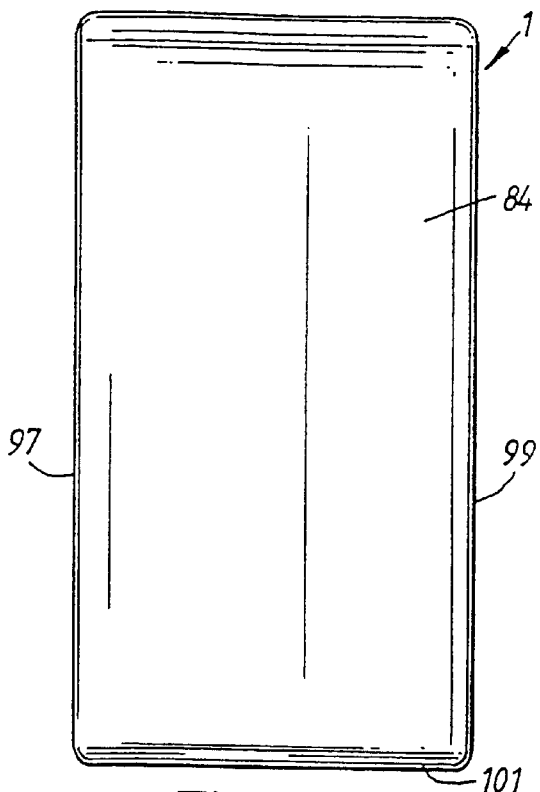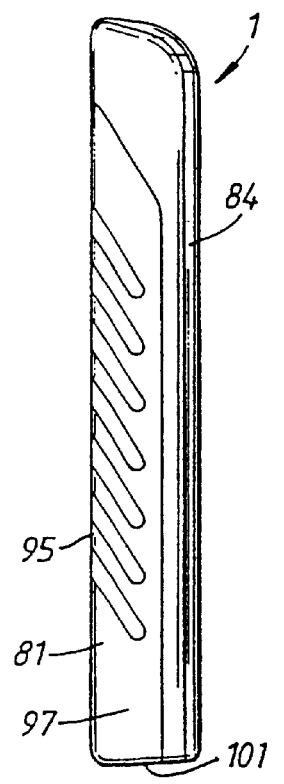
Fig.20(a)     Fig.20(b)
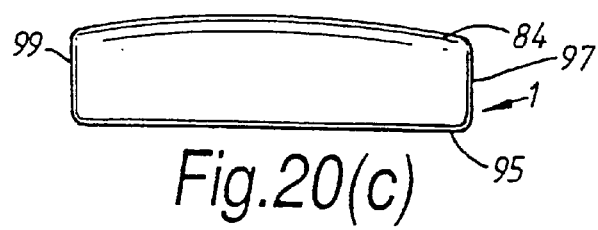
Fig.20(c)
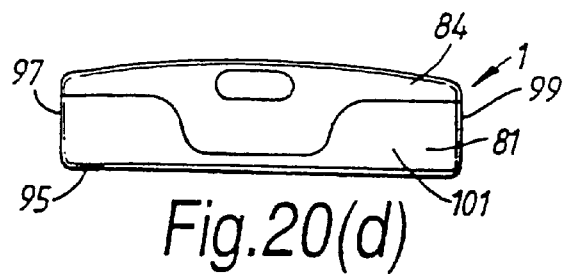
Fig.20(d)

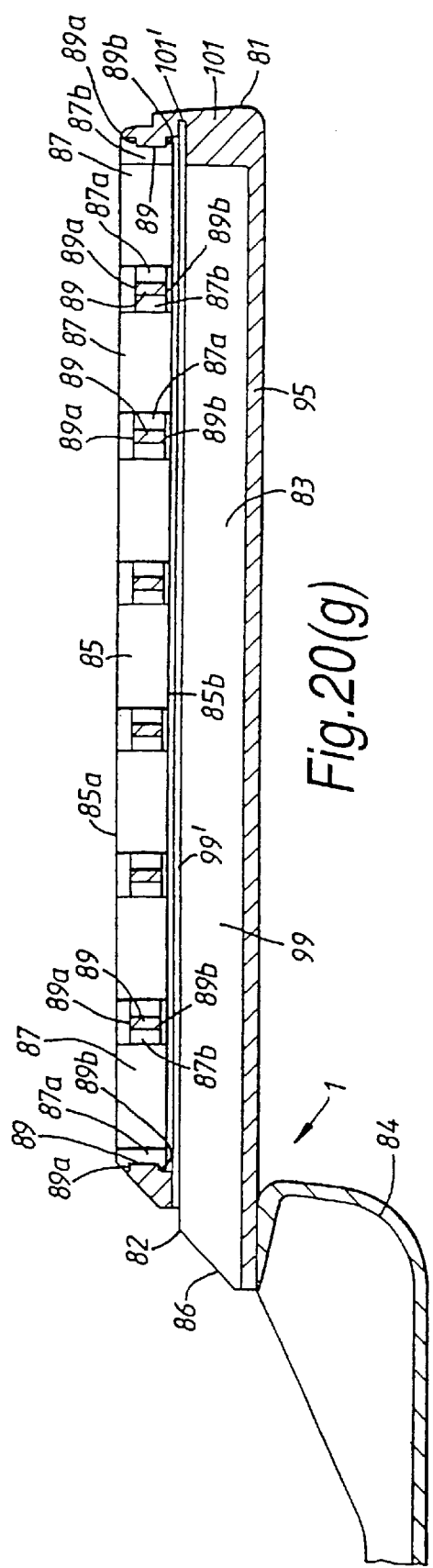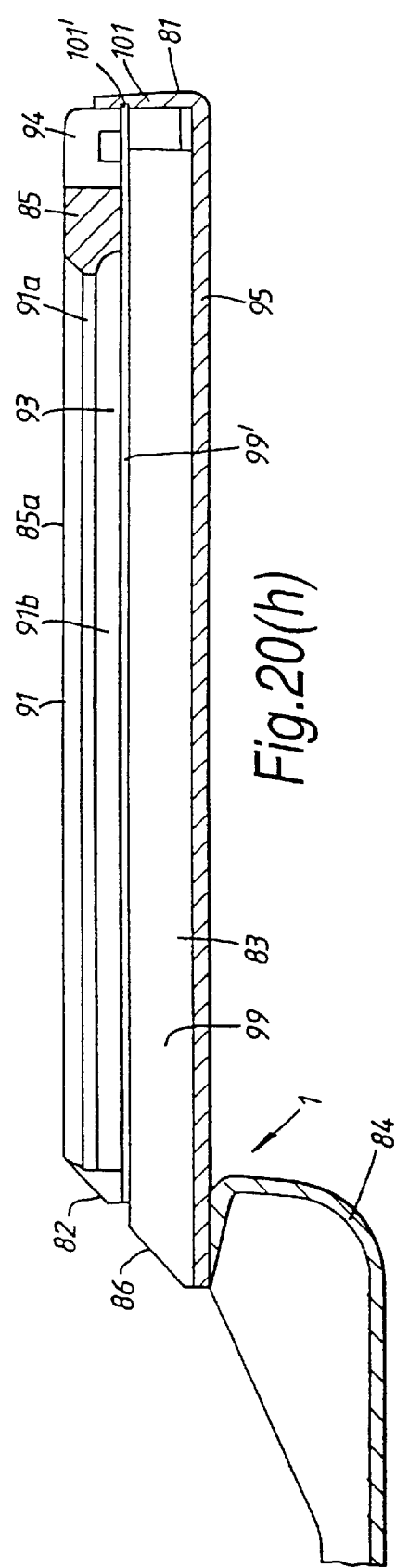

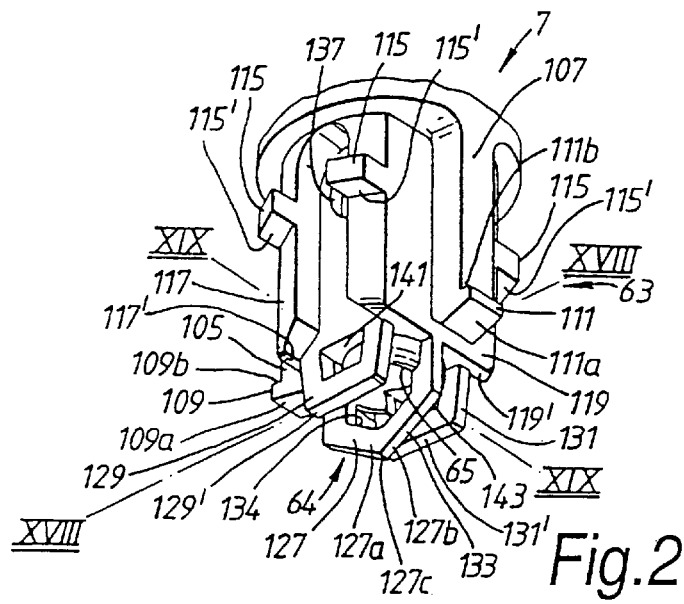
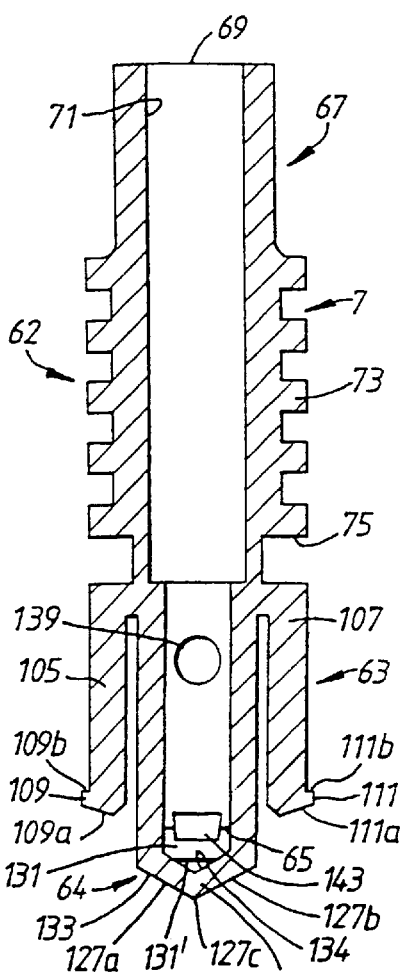
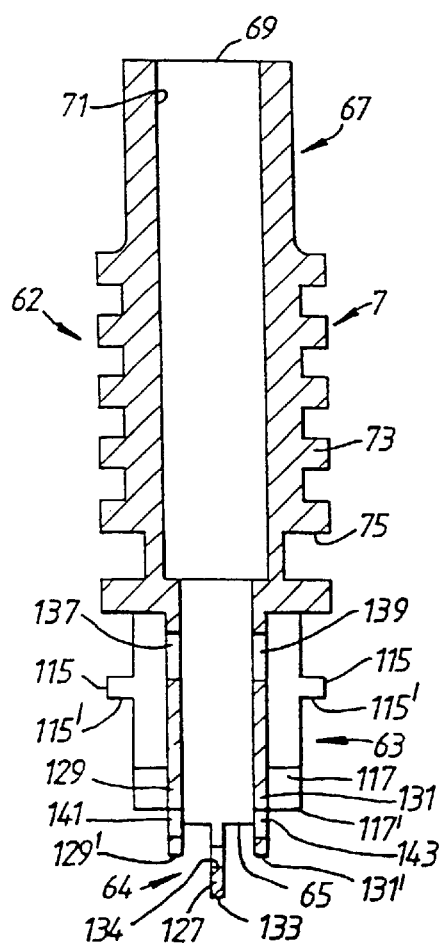
Fig.26(a)
Fig.26(b)
Fig.26(c)

INHALATION DEVICE

The present invention relates to an inhaler, more particularly an inhaler for administering dry powder by inhalation, and a blister pack assembly for an inhaler.

It is known in the treatment of respiratory conditions, such as asthma, to provide certain medicaments in the form of a dry powder for inhalation. It is also known to provide individual doses of such powders in the blisters of a blister pack element.

WO-A-97/40876 discloses an inhaler for administering dry powder by inhalation which comprises a support unit for supporting a blister pack element having a plurality of blisters formed therein, with each blister containing a dose of powder containing medicament, and a suction tube configured so as to be insertable into a respective one of the blisters and through which a dose of powder is in use drawn on inhalation by a user. The support unit of this inhaler includes a chamber having a hinged lid for holding the suction tube when not in use.

It is an aim of the present invention to provide such an inhaler and a blister pack assembly therefor which are of improved construction so as to facilitate ease of operation by a user.

The present invention provides a blister pack assembly for an inhaler for administering powder containing medicament by inhalation, comprising: a suction tube through which powder is in use drawn on inhalation by a user; and a blister pack unit comprising a blister pack element which includes a plurality of blisters, each containing a dose of powder containing medicament, and an attachment member disposed to one side of the blister pack element to which the suction tube is attachable when not in use.

Preferably, the attachment member includes at least one attachment element which is configured resiliently to hold the suction tube.

More preferably, the attachment member includes first and second attachment elements which are configured such that when the suction tube is attached to one of the first and second attachment elements the other of the first and second attachment elements acts as a guard to protect part of the suction tube.

Preferably, each attachment element is a resilient clip.

Preferably, the blister pack assembly further comprises an interconnecting member for connecting the suction tube to the blister pack unit.

Preferably, the interconnecting member is movably coupled to the suction tube.

More preferably, the interconnecting member includes a clip to which the suction tube is rotatably coupled.

Preferably, the interconnecting member includes an element which is slideably disposed to the blister pack unit.

In one embodiment the blister pack unit includes an elongate track in which the element of the interconnecting member is captively slideably disposed.

Preferably, the elongate track extends along the longitudinal axis of the blister pack unit In another embodiment the blister pack unit includes an elongate channel and the element of the interconnecting member in use is slideably disposed in the channel.

Preferably, the elongate channel extends along the longitudinal axis of the blister pack unit.

Preferably, the blister pack unit includes at least one moisture permeable chamber which contains a desiccant.

More preferably, the at least one moisture permeable chamber is disposed between cavities of the blisters.

Preferably, the suction tube comprises an elongate body which includes an inlet section at one end thereof, which inlet section includes an inlet and a cutting assembly comprising a cutting blade which includes a cutting edge for making a cut in the covering film of a blister and at least one ram blade which includes a bearing surface for bearing on the covering film of the blister and pushing the same into the cavity of the blister, an outlet section at the other end thereof, which outlet section includes an outlet and provides a mouthpiece, and an inhalation channel providing fluid communication between the inlet and the outlet through which powder is in use drawn on inhalation by a user.

Preferably, each ram blade includes at least one transverse opening.

In one embodiment the at least one transverse opening is axially rearward of the bearing surface of the ram blade.

In another embodiment the at least one transverse opening extends axially rearwardly from the bearing surface of the ram blade.

Preferably, the at least one transverse opening is asymmetrically located in the ram blade.

Preferably, the at least one ram blade is substantially planar.

Preferably, the inlet section of the suction tube includes supplementary air inlet openings into the inhalation channel at an axial position rearwardly adjacent the inlet.

Preferably, the cutting assembly of the suction tube includes first and second ram blades disposed on opposite sides of the cutting blade.

More preferably, each ram blade is disposed substantially the same radial distance from the cutting blade.

Preferably, the cutting assembly of the suction tube is configured such that the distance between the endmost points of the bearing surface of each of the ram blades is approximately the same distance as the distance between the endmost points of the effective cutting length of the cutting blade and the adjacent endmost points of the bearing surface of each of the ram blades.

Preferably, the axial position of the inlet is such that when the inlet section is located in a blister the inlet is located below the surface defining the opening of the cavity of the blister.

The present invention also extends to an inhaler for administering powder containing medicament by inhalation which comprises the above-described blister pack assembly.

Preferably, the inhaler further comprises a support unit for supporting the blister pack assembly.

More preferably, the support unit includes a wall member which includes a plurality of openings adjacent which the blister pack element of the blister pack assembly is in use disposed such that a blister is located beneath each opening.

Preferably, the support unit includes an elongate slot which together with the elongate channel in the blister pack unit defines an elongate track in which the element of the interconnecting member is captively slideably disposed.

More preferably, the elongate slot extends along the longitudinal axis of the support unit.

Preferably, the elongate slot includes a narrow section through which the element of the interconnecting member cannot pass.

Preferably, the elongate slot is located in the wall member of the support unit.

The present invention also provides an inhaler for administering powder containing medicament by inhalation, comprising: a suction tube through which powder is in use drawn on inhalation by a user; a support unit for supporting a blister pack element which includes a plurality of blisters, each containing a dose of powder containing medicament; and an interconnecting member correcting the suction tube to the support unit, wherein the interconnecting member includes an element which is slideably disposed to the support Preferably, the support unit includes an elongate track in which the element of the interconnecting member is captively slideably disposed.

Preferably, the interconnecting member is movably coupled to the suction tube.

More preferably, the interconnecting member includes a clip to which the suction tube is rotatably coupled Preferably, the suction tube comprises an elongate body which includes an inlet section at one end thereof, which inlet section includes an inlet and a cutting assembly comprising a cutting blade which includes a cutting edge for making a cut in the covering film of a blister and at least one ram blade which includes a bearing surface for bearing on the covering film of the blister and pushing the same into the cavity of the blister, an outlet section at the other end thereof, which outlet section includes an outlet and provides a mouthpiece, and an inhalation channel providing fluid communication between the inlet and the outlet through which powder is in use drawn on inhalation by a user.

The present invention further provides a blister pack assembly for an inhaler for administering powder containing medicament by inhalation, comprising: a suction tube through which powder is in use drawn on inhalation by a user; a blister pack element which includes a plurality of blisters, each containing a dose of powder containing medicament; and an interconnecting member connecting the suction tube to the blister pack element, wherein the interconnecting member includes an element which is slideably disposed to the blister pack element.

Preferably, the interconnecting member is movably coupled to the suction tube.

More preferably, the interconnecting member includes a clip to which the suction tube is rotatably coupled.

In one embodiment the blister pack element includes an elongate track in which the element of the interconnecting member is captively slideably disposed.

Preferably, the elongate track extends along the longitudinal axis of the blister pack element.

In another embodiment the blister pack element includes an elongate channel and the element of the interconnecting member in use is slideably disposed in the channel.

Preferably, the elongate channel extends along the longitudinal axis of the blister pack element.

Preferably, the blister pack element includes at least one moisture permeable chamber which contains a desiccant.

More preferably the at least one moisture permeable chamber is disposed between cavities of the blisters.

Preferably, the suction tube comprises an elongate body which includes an inlet section at one end thereof, which inlet section includes an inlet and a cutting assembly comprising a cutting blade which includes a cutting edge for making a cut in the covering film of a blister and at least one ram blade which includes a bearing surface for bearing on the covering film of the blister and pushing the same into the cavity of the blister, an outlet section at the other end thereof, which outlet section includes an outlet and provides a mouthpiece, and an inhalation channel providing fluid communication between the inlet and the outlet through which powder is in use drawn on inhalation by a user.

The present invention also extends to an inhaler for administering powder containing medicament by inhalation which comprises the above-described blister pack assembly.

Preferably, the inhaler further comprises a support unit for supporting the blister pack assembly.

More preferably, the support unit includes a wall member which includes a plurality of openings adjacent which the blister pack element of the blister pack assembly is in use disposed such that a blister is located beneath each opening.

Preferably, the support unit includes an elongate slot which together with the elongate channel in the blister pack element defines an elongate track in which the element of the interconnecting member is captively slideably disposed More preferably, the elongate slot extends along the longitudinal axis of the support unit.

Preferably, the elongate slot includes a narrow section through which the element of the interconnecting member cannot pass.

Preferably the elongate slot is located in the wall member of the support unit.

Medicaments suitable for administration by the powder inhaler of the present invention are any which may be delivered by inhalation and include, for example, β2-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers: cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

Preferred embodiments of the present invention will now be described hereinbelow by way of example only with reference to the accompanying drawings, in which:

FIG. 16(a) illustrates in enlarged scale a plan view of the blister pack element of the blister pack assembly of FIG. 12;

FIG. 16(b) illustrates an underneath plan view of the blister pack element of FIG. 16(a);

FIG. 16(c) illustrates a side view of the blister pack element of FIG. 16(a);

FIG. 16(d) illustrates one end view of the blister pack element of FIG. 16(a);

FIG. 16(e) illustrates the other end view of the blister pack element of FIG. 16(a);

FIG. 16(f) illustrates a vertical sectional view (along section VI—VI in FIG. 16(a)) of the blister pack element of FIG. 16(a);

FIG. 16(g) illustrates a vertical sectional view (along section VII—VII in FIG. 16(a)) of the blister pack element of FIG. 16(a);

FIG. 20(a) illustrates a plan view of the support unit of the inhaler of FIG. 1, illustrated in the closed or storage configuration;

FIG. 20(b) illustrates a side view of the support unit of FIG. 20(a), illustrated in the closed or storage configuration;

FIG. 20(c) illustrates one end view of the support unit of FIG. 20(a), illustrated in the closed or storage configuration;

FIG. 20(d) illustrates the other end view of the support unit of FIG. 20(a), illustrated in the closed or storage configuration;

FIG. 20(g) illustrates in enlarged scale a fragmentary vertical sectional view (along section X—X in FIG. 20(e)) of the support unit of FIG. 20(a), illustrated in the open or operative configuration;

FIG. 20(h) illustrates in enlarged scale a fragmentary vertical sectional view (along section XI—XI in FIG. 20(e)) of the support unit of FIG. 20(a), illustrated in the open or operative configuration;

FIG. 26(a) illustrates a fragmentary perspective view of a third modified suction tube for the inhaler of FIG. 1;

FIG. 26(b) illustrates a vertical sectional view (along section XX—XX in FIG. 26(a)) of the suction tube of FIG. 26(a);

FIG. 26(c) illustrates a vertical sectional view (along section XXI—XXI in FIG. 26(a)) of the suction tube of FIG. 26(a);

Figure 1:
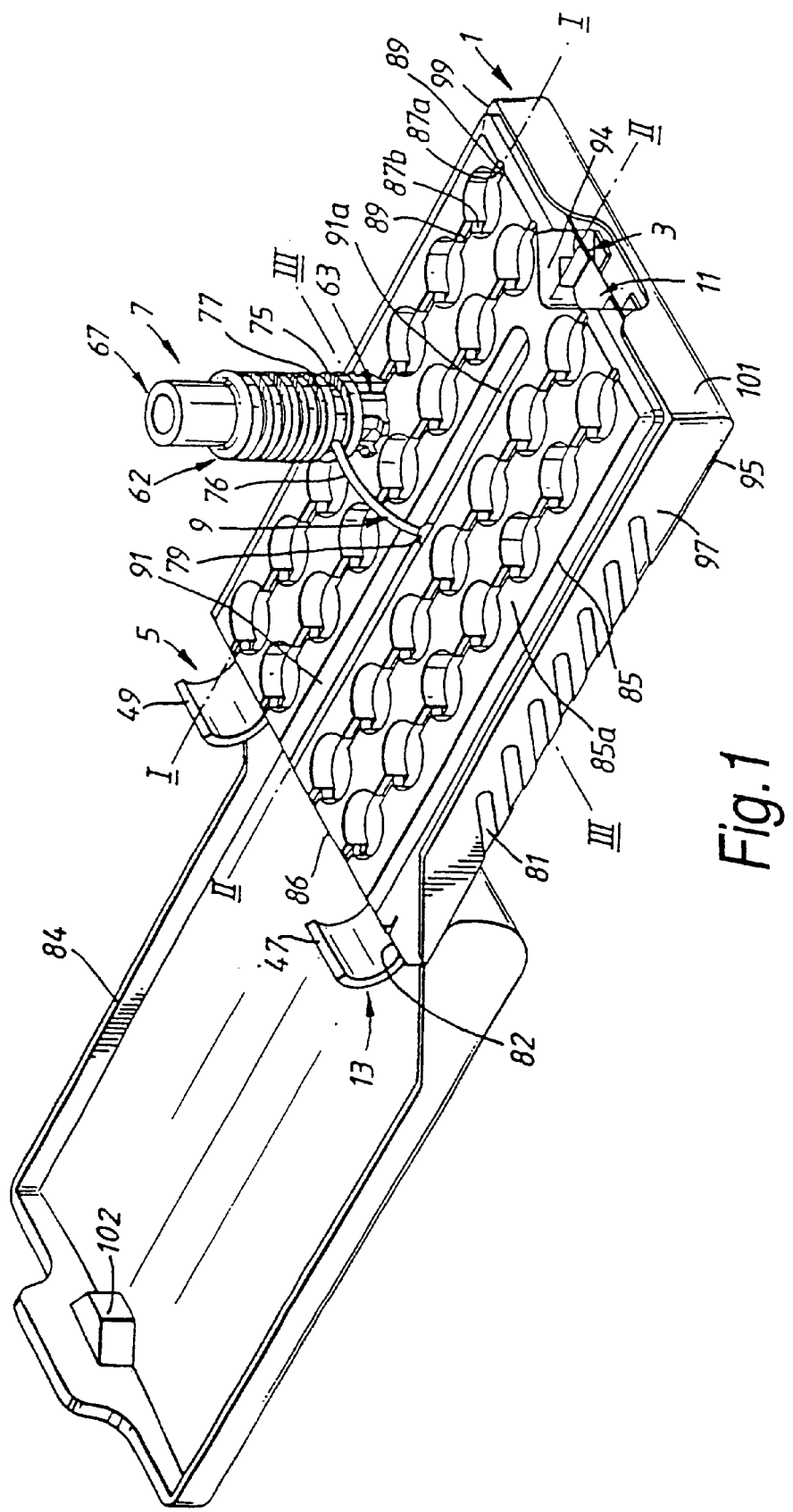
FIG. 1 illustrates in use a perspective view of an inhaler in accordance with a preferred embodiment of the present invention.
Figure 2:
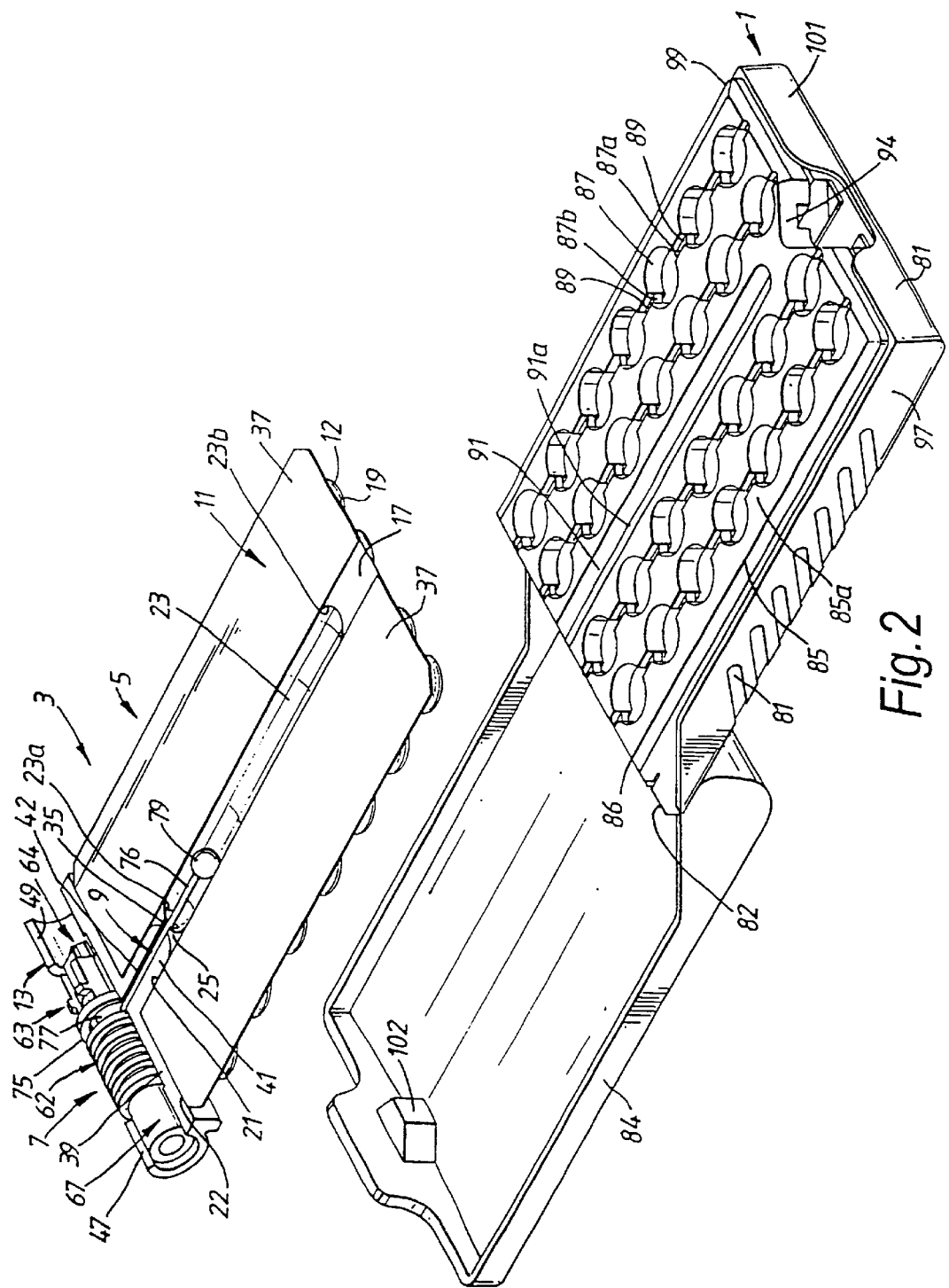
FIG. 2 illustrates an exploded perspective view of the inhaler of FIG. 1.
Figure 3:
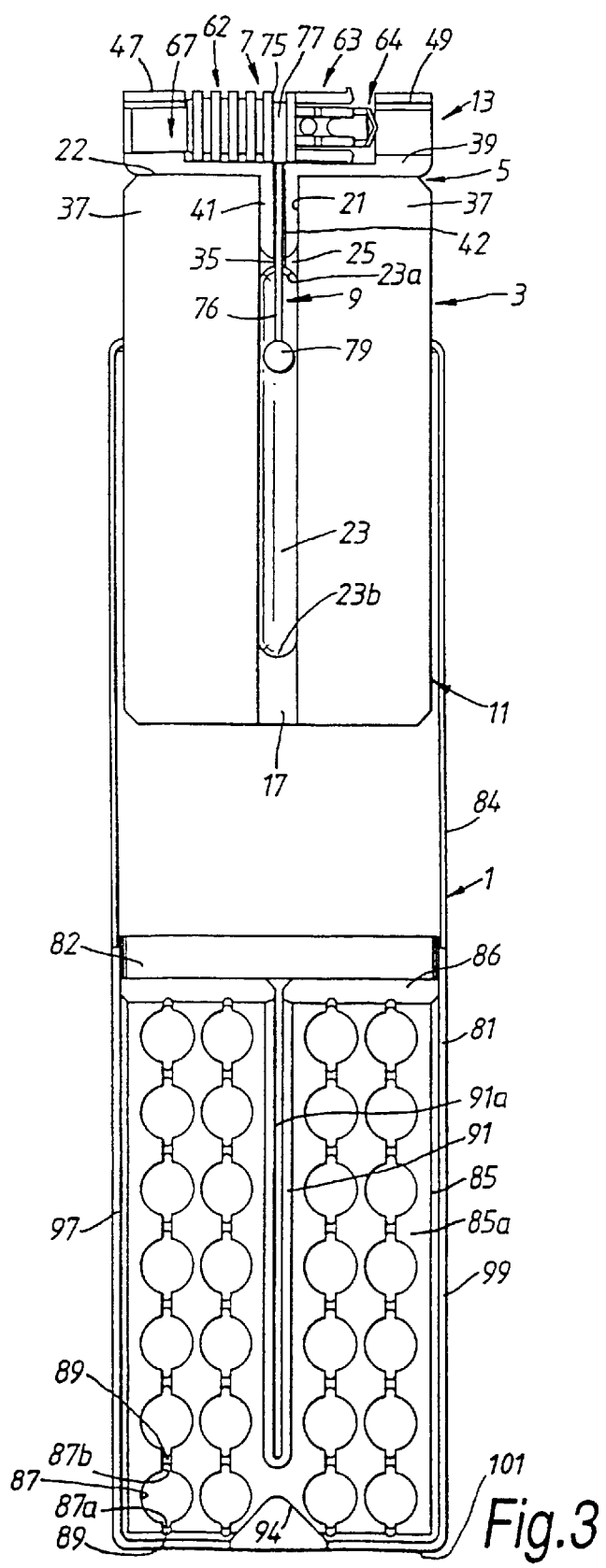
FIG. 3 illustrates a plan view of the inhaler of FIG. 1, illustrated with the blister pack assembly separated from the support unit.
Figure 4:
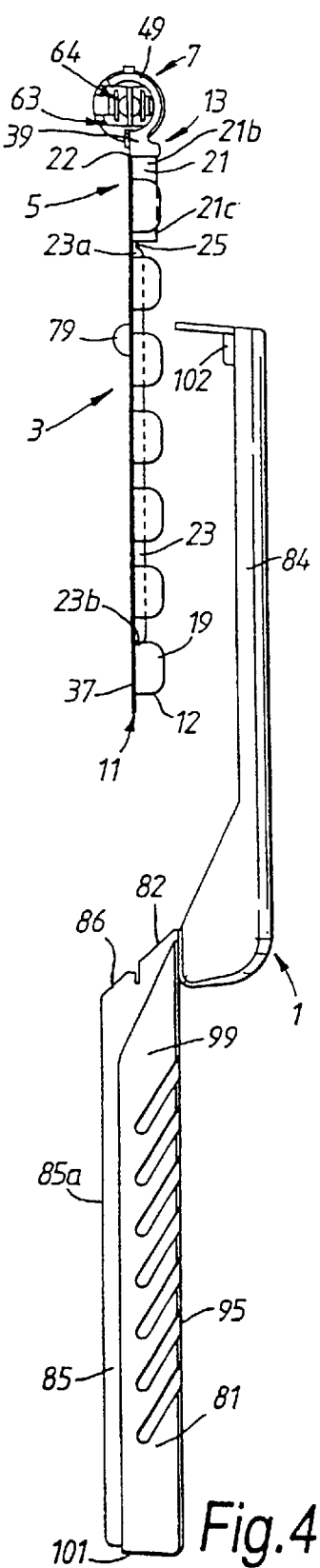
FIG. 4 illustrates a side view of the inhaler of FIG. 1, illustrated with the blister pack assembly separated from the support unit.
Figure 5:
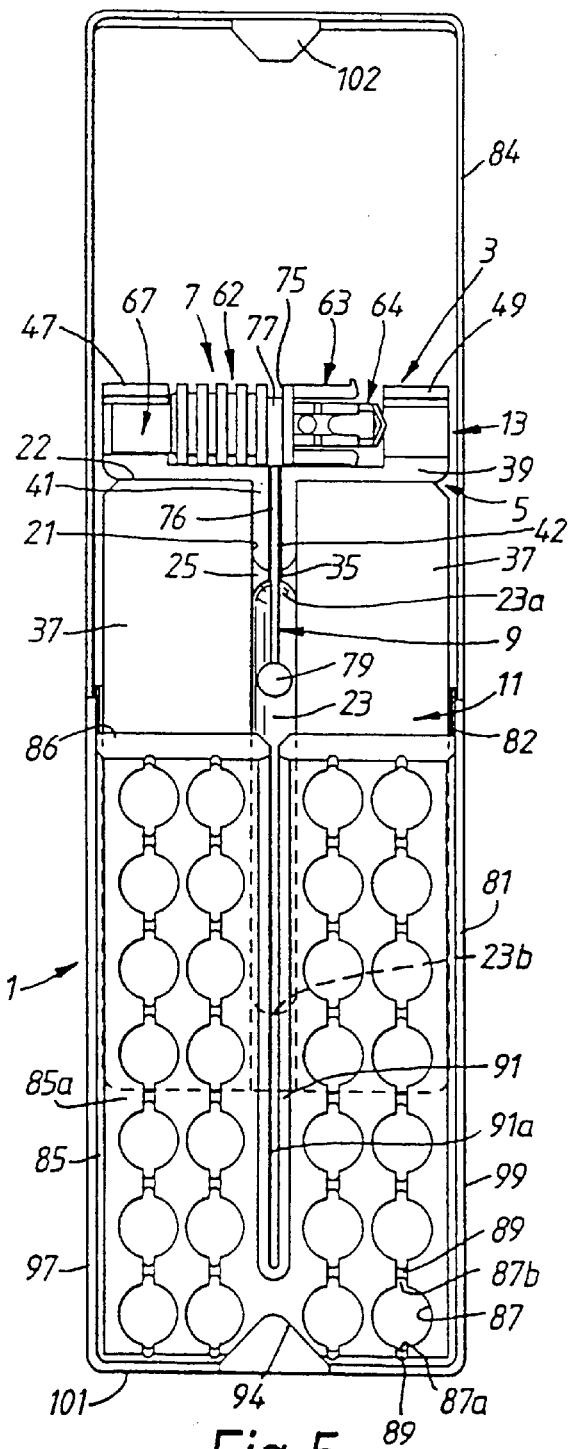
FIG. 5 illustrates a plan view of the inhaler of FIG. 1, illustrated with the blister pack assembly partially loaded into/unloaded from the support unit.
Figure 6:
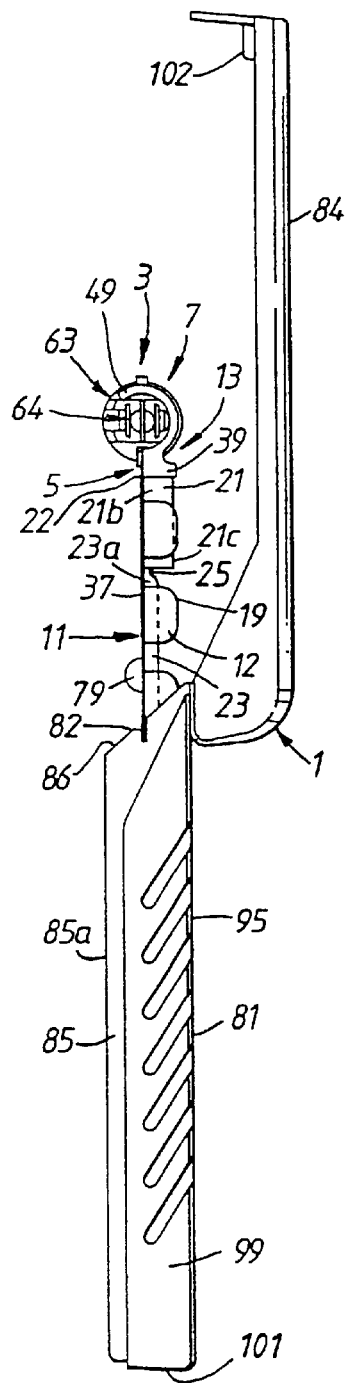
FIG. 6 illustrates a side view of the inhaler of FIG. 1, illustrated with the blister pack assembly partially loaded into/unloaded from the support unit.
Figure 7:
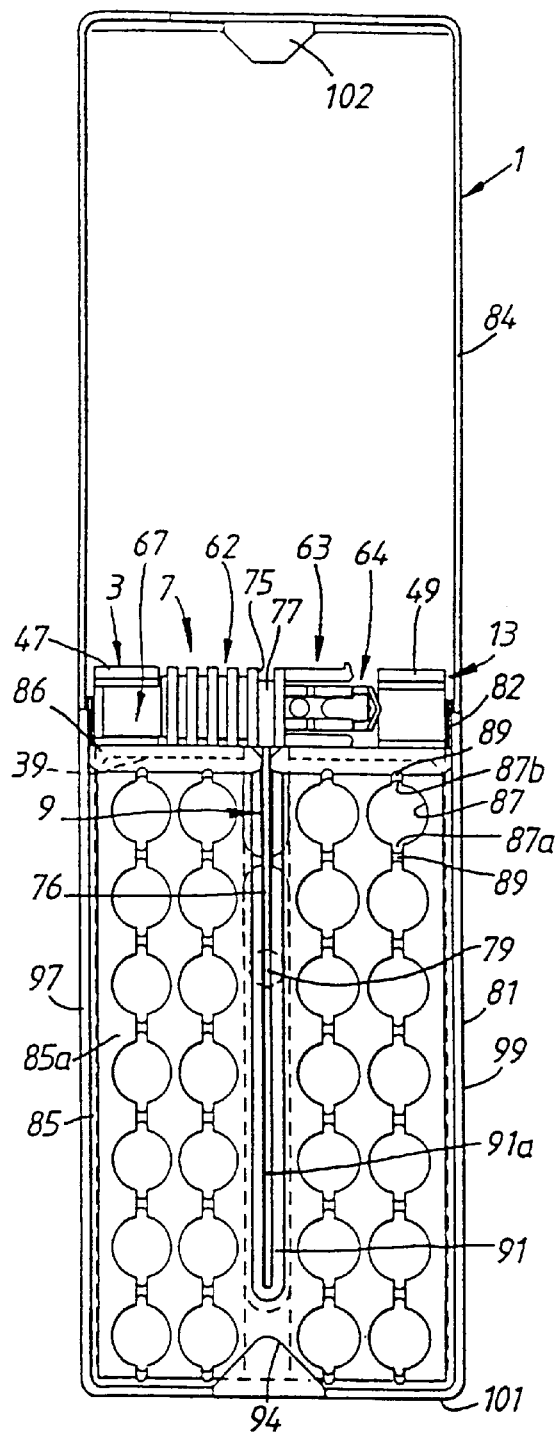
FIG. 7 illustrates a plan view of the inhaler of FIG. 1, illustrated with the blister pack assembly loaded in the support unit.
Figure 8:
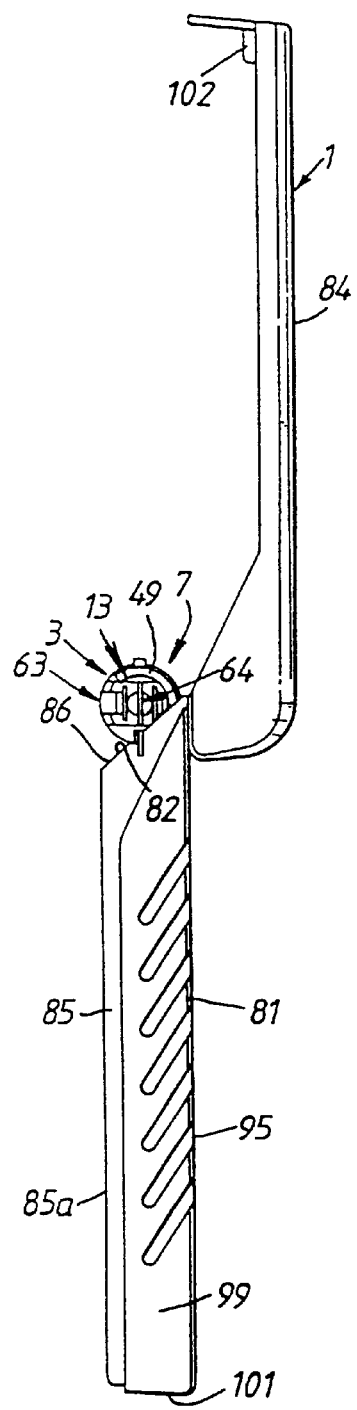
FIG. 8 illustrates a side view of the inhaler of FIG. 1, illustrated with the blister pack assembly loaded in the support unit.
Figure 9:
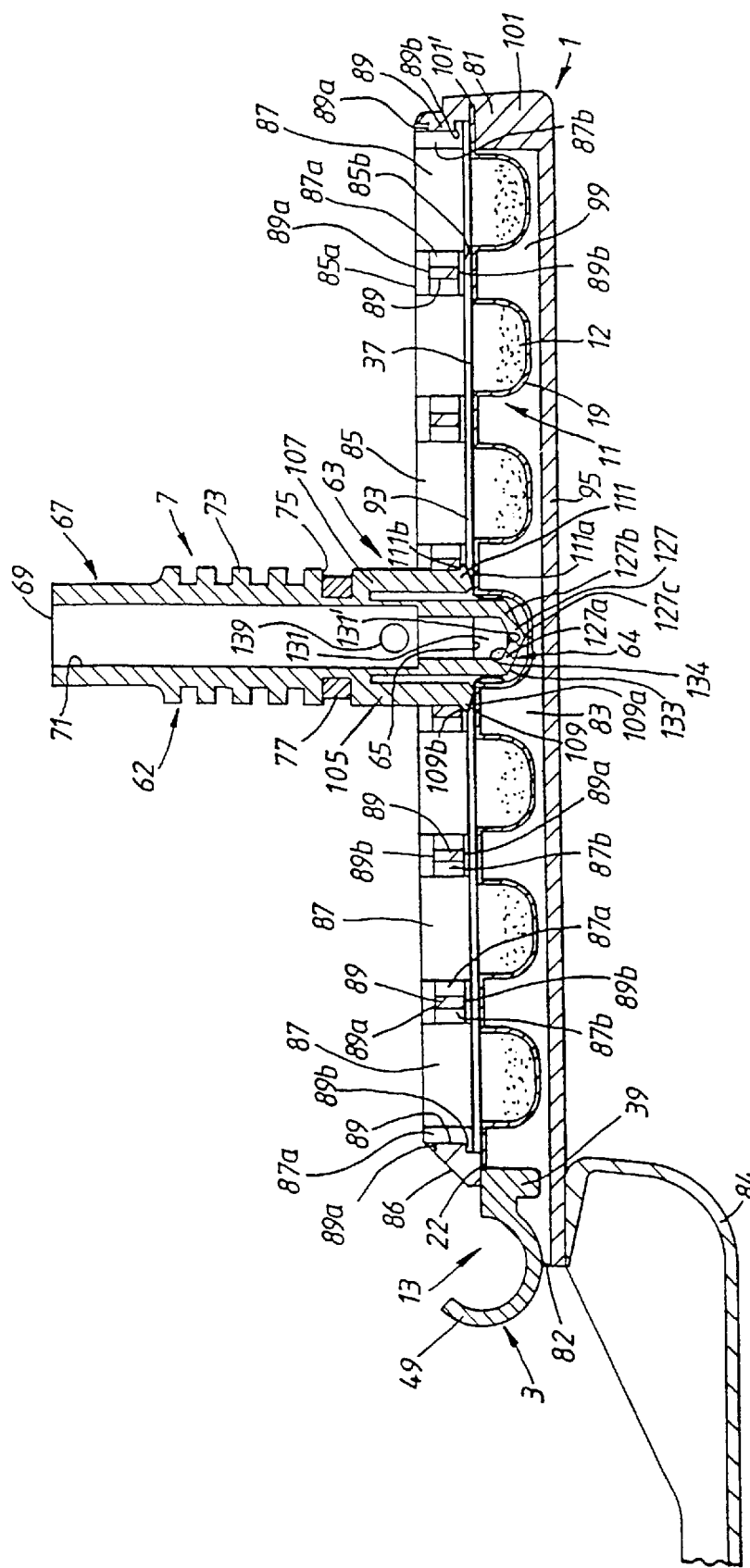
FIG. 9 illustrates in enlarged scale a fragmentary vertical sectional view (along section I—I in FIG. 1) of the inhaler of FIG. 1.
Figure 10:
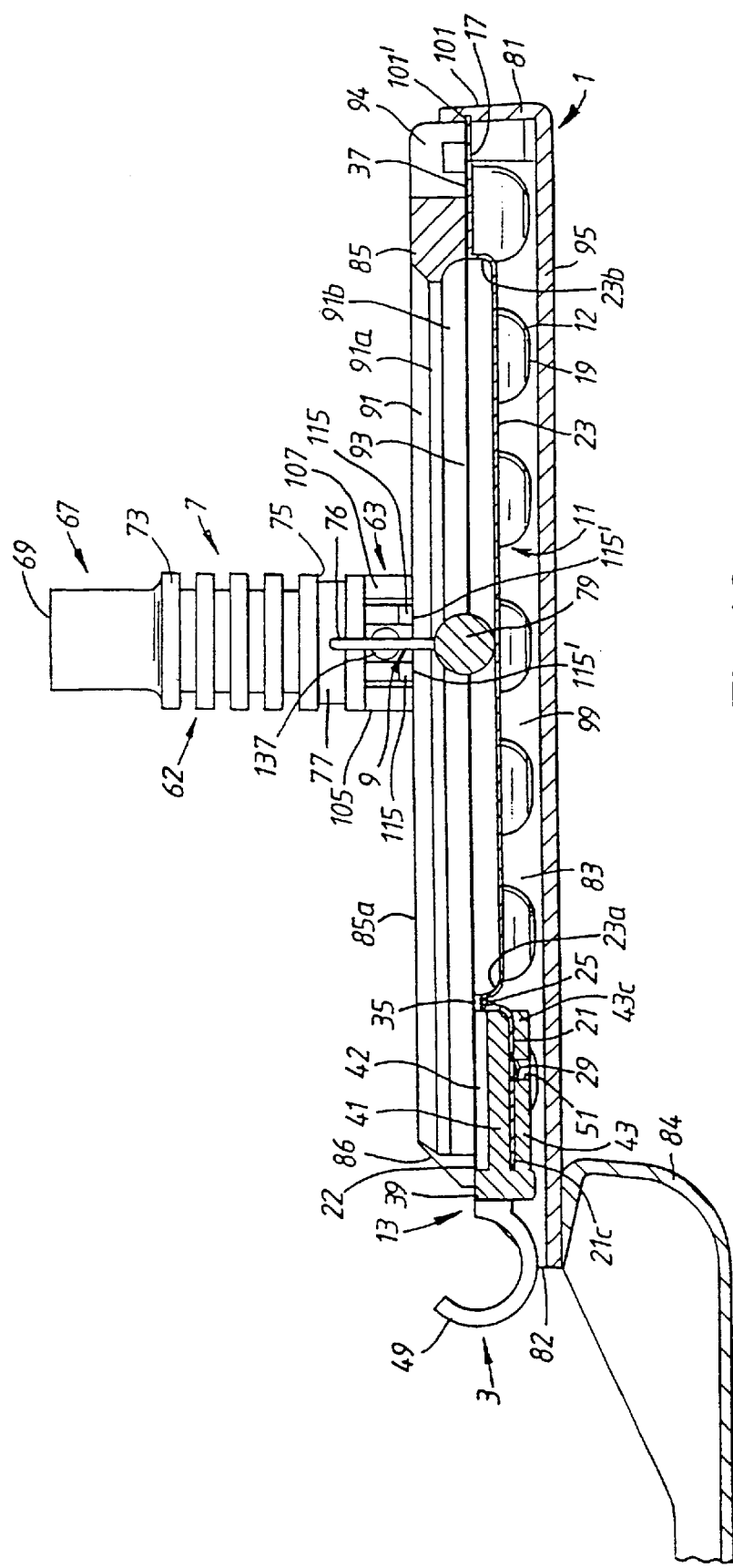
FIG. 10 illustrates in enlarged scale a fragmentary vertical sectional view (along section II—II in FIG. 1) of the inhaler of FIG. 1.
Figure 11:
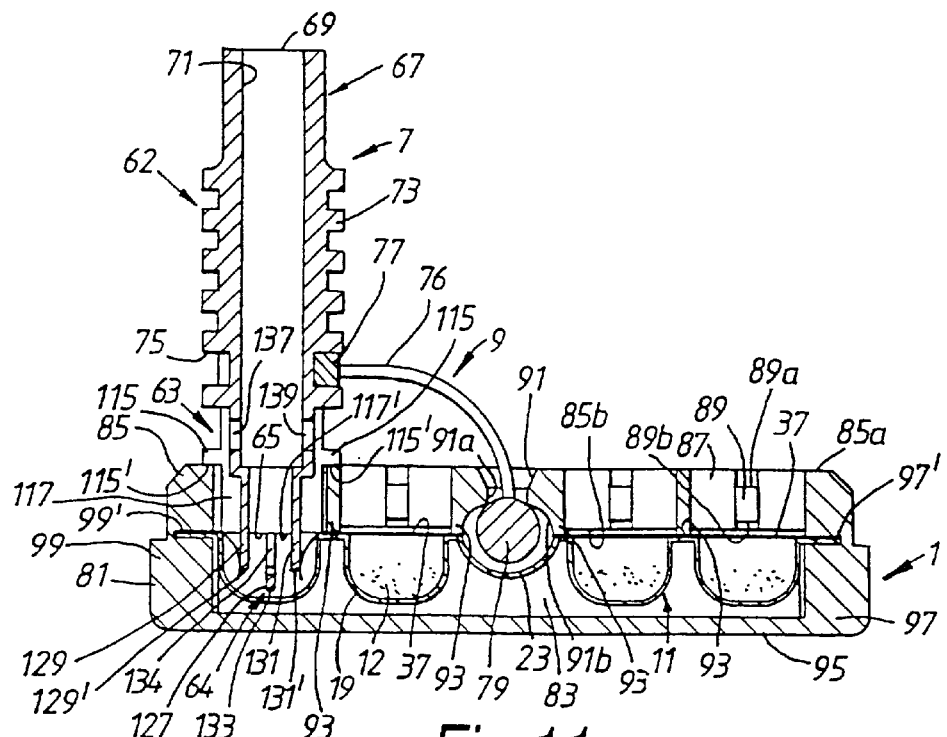
FIG. 11 illustrates in enlarged a fragmentary vertical sectional view (along section III—III in FIG. 1) of the inhaler of FIG. 1.
Figure 12:
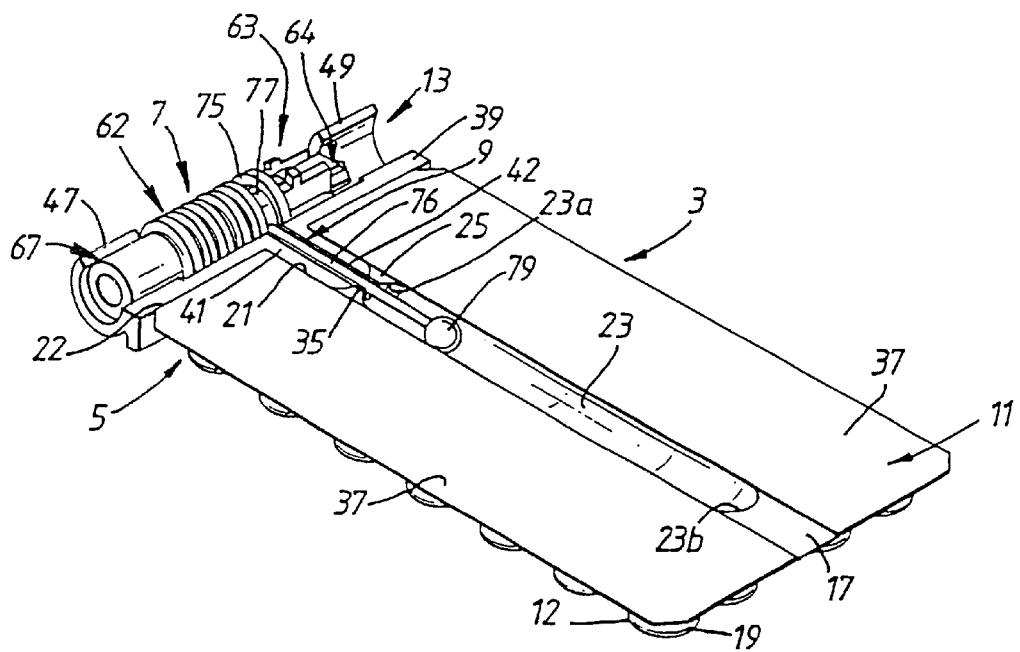
FIG. 12 illustrates a perspective view of the blister pack assembly of the inhaler of FIG. 1.
Figure 13:
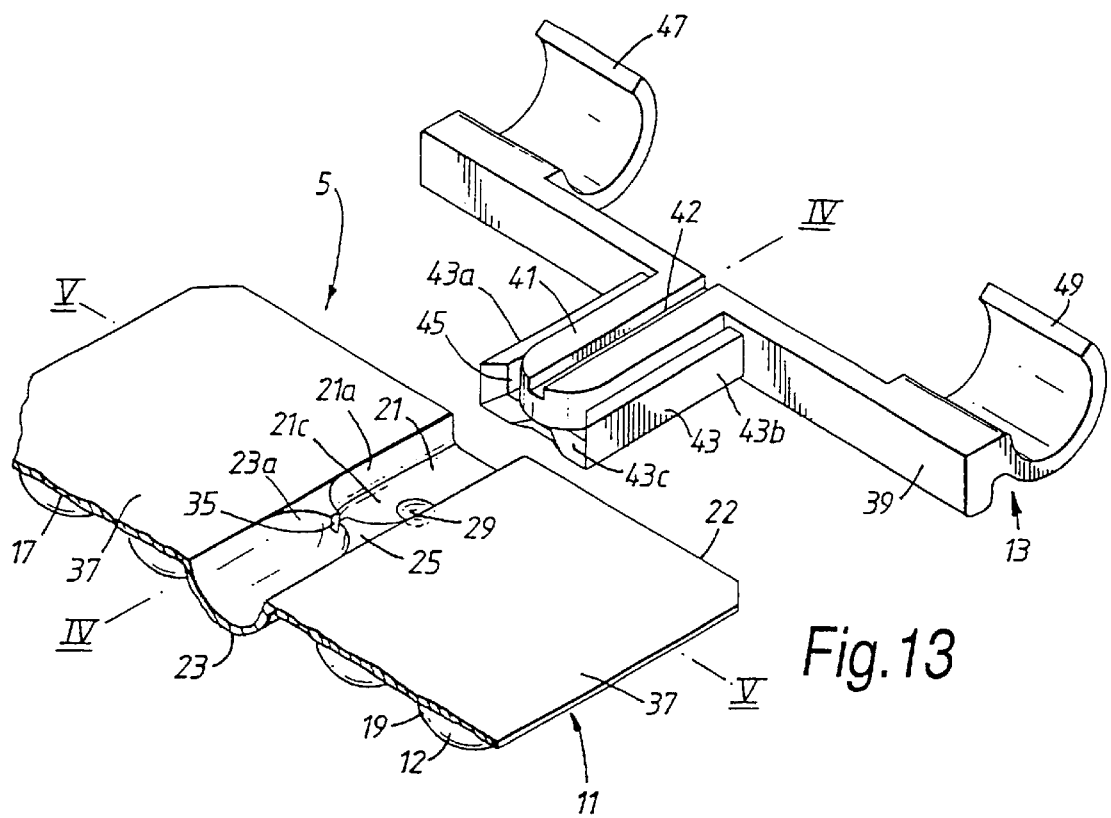
FIG. 13 illustrates in enlarged scale a fragmentary exploded perspective view of the blister pack unit of the blister pack assembly of FIG. 12.
Figure 14:
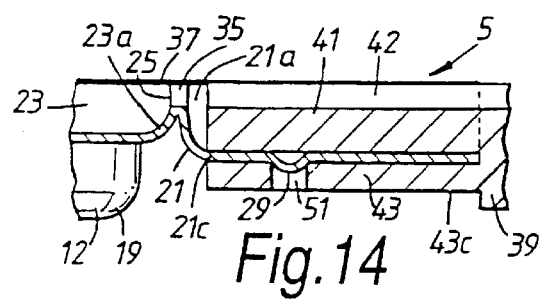
FIG. 14 illustrates a fragmentary vertical sectional view (along section IV—IV in FIG. 13) of the blister pack unit of FIG. 13.
Figure 15:
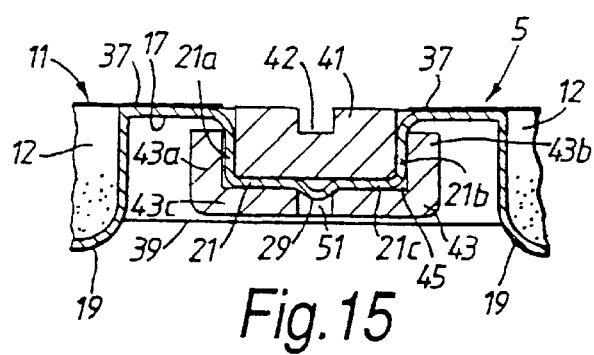
FIG. 15 illustrates a fragmentary vertical sectional view (along section V—V in FIG. 13) of the blister pack unit of FIG. 13.
Figure 17A:
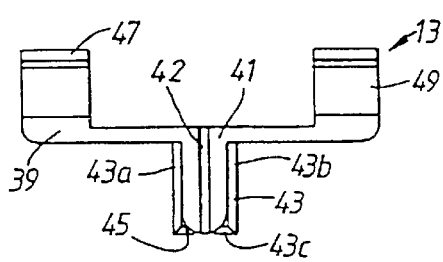
FIG. 17(a) illustrates in enlarged scale a plan view of the attachment member of the blister pack unit of the blister pack assembly of FIG. 12.
Figure 17B:
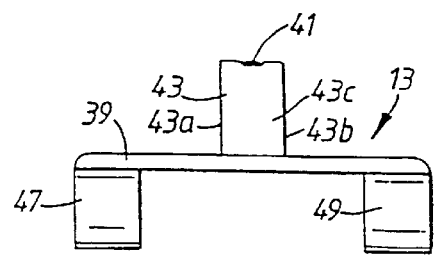
FIG. 17(b) illustrates an underneath plan view of the attachment member of FIG. 17(a)
Figure 17C:
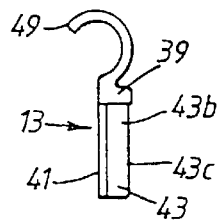
FIG. 17(c) illustrates an end view of the attachment member of FIG. 17(a)
Figure 17D:
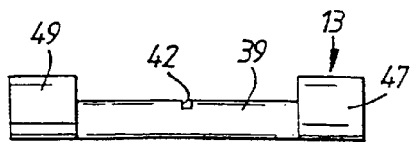
FIG. 17(d) illustrates one side view of the attachment member of FIG. 17(a)
Figure 17E:
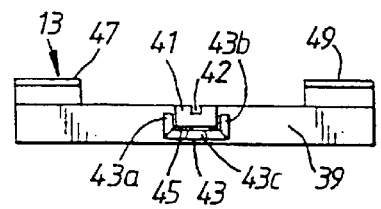
FIG. 17(e) illustrates the other side view of the attachment member of FIG. 17(a)
Figure 19A:
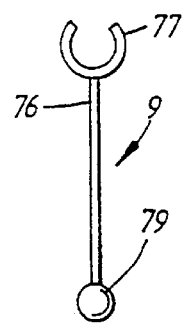
FIG. 19(a) illustrates a plan view of the interconnecting member of the blister pack assembly of FIG. 12.
Figure 19B:
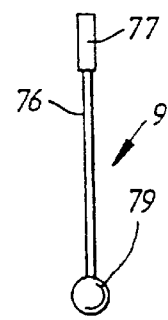
FIG. 19(b) illustrates a side view of the interconnecting member of FIG. 19(a)
Figure 18A:
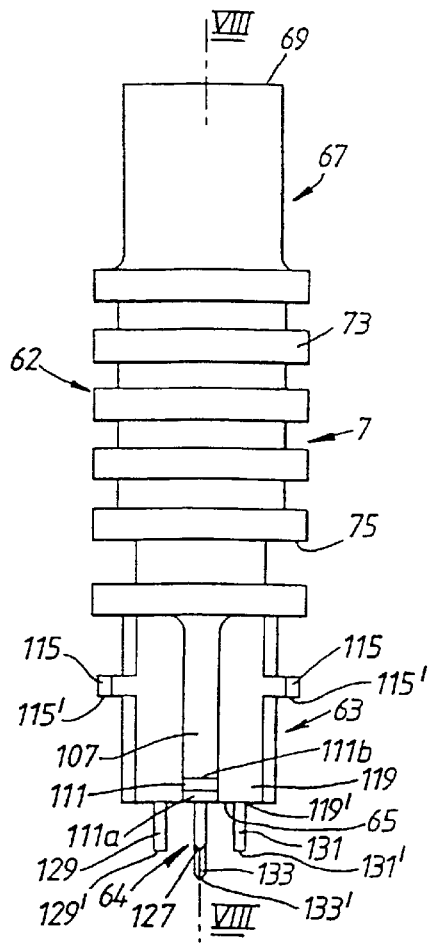
FIG. 18(a) illustrates in enlarged scale a first side view of the suction tube of the blister pack assembly of FIG. 12.
Figure 18B:
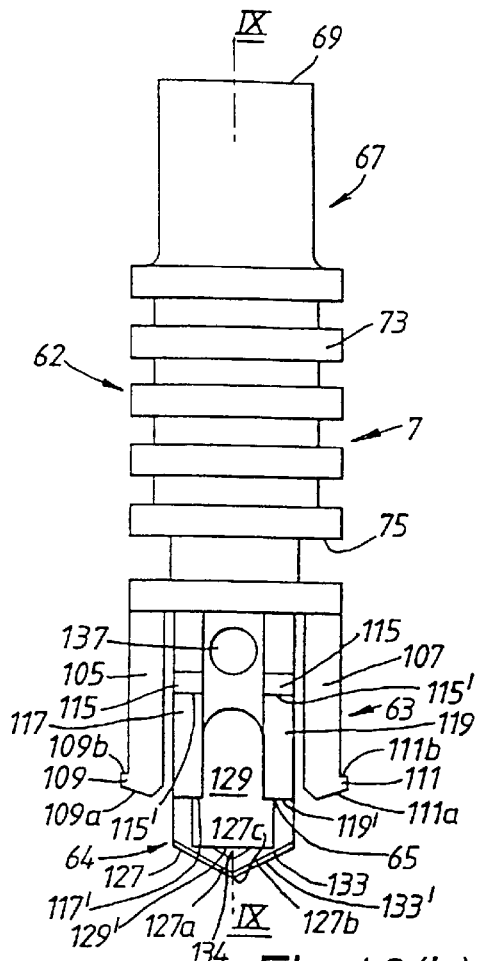
FIG. 18(b) illustrates a second, orthogonal side view of the suction tube of FIG. 18(a)
Figure 18C:
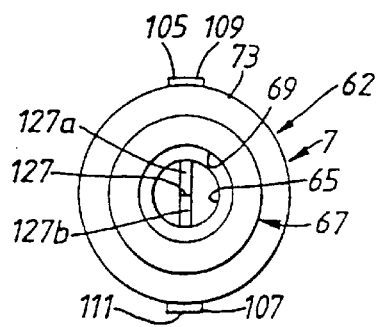
FIG. 18(c) illustrates a plan view of the suction tube of FIG. 18(a)
Figure 18D:
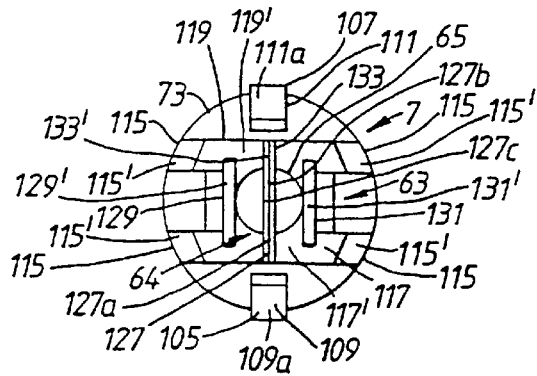
FIG. 18(d) illustrates an underneath plan view of the suction tube of FIG. 18(a)
Figure 18E:
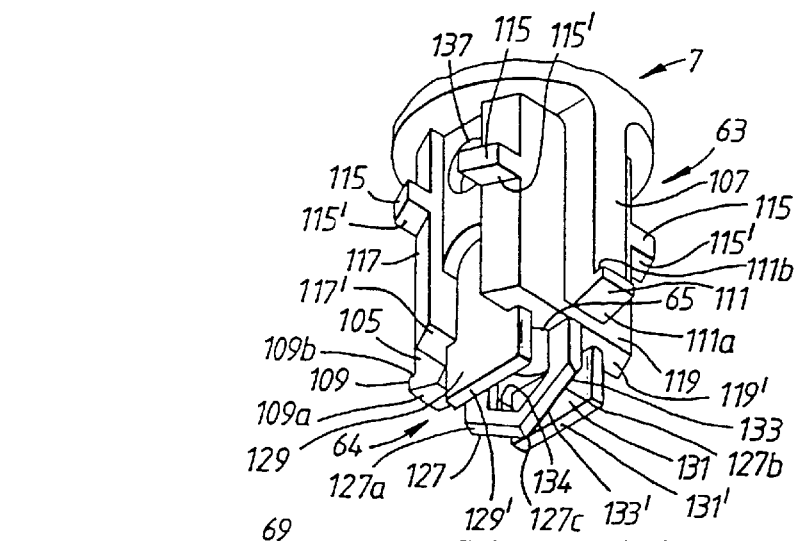
FIG. 18(e) illustrates a fragmentary perspective view of the suction tube of FIG. 18(a)
Figure 18F:
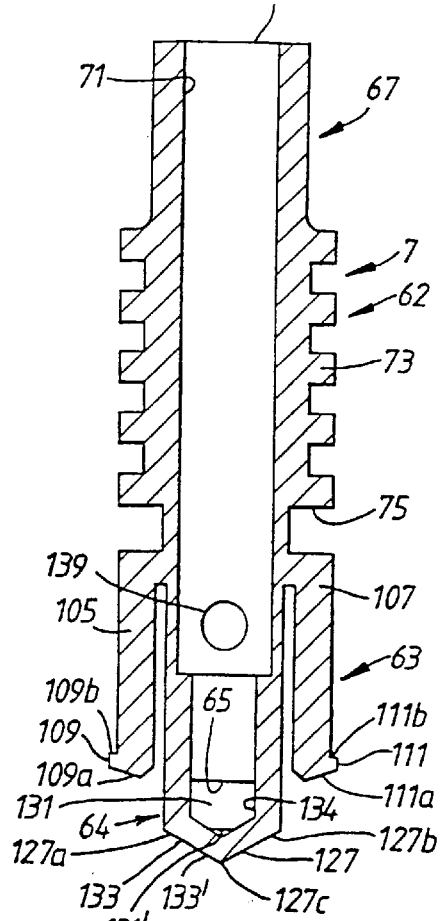
FIG. 18(f) illustrates a vertical sectional view (along section VIII—VIII in FIG. 18(a)) of the suction tube of FIG. 18(a)
Figure 18G:
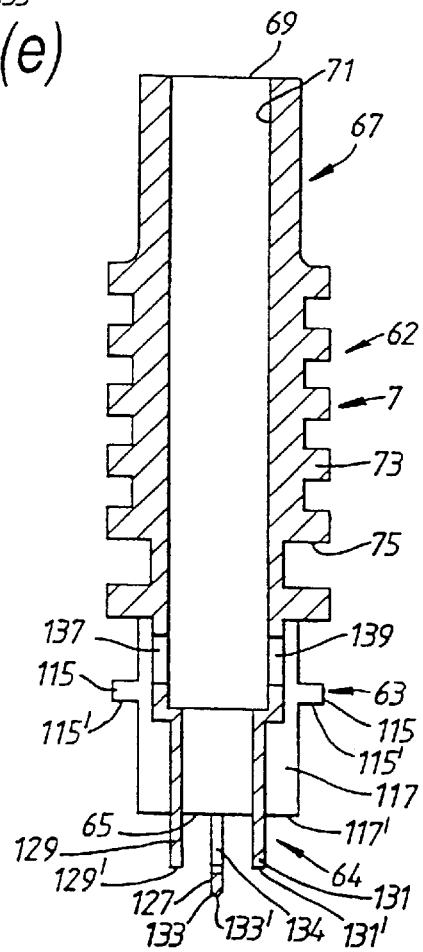
FIG. 18(g) illustrates a vertical sectional view (along section IX—IX in FIG. 18(b)) of the suction tube of FIG. 18(a)
Figure 20E:
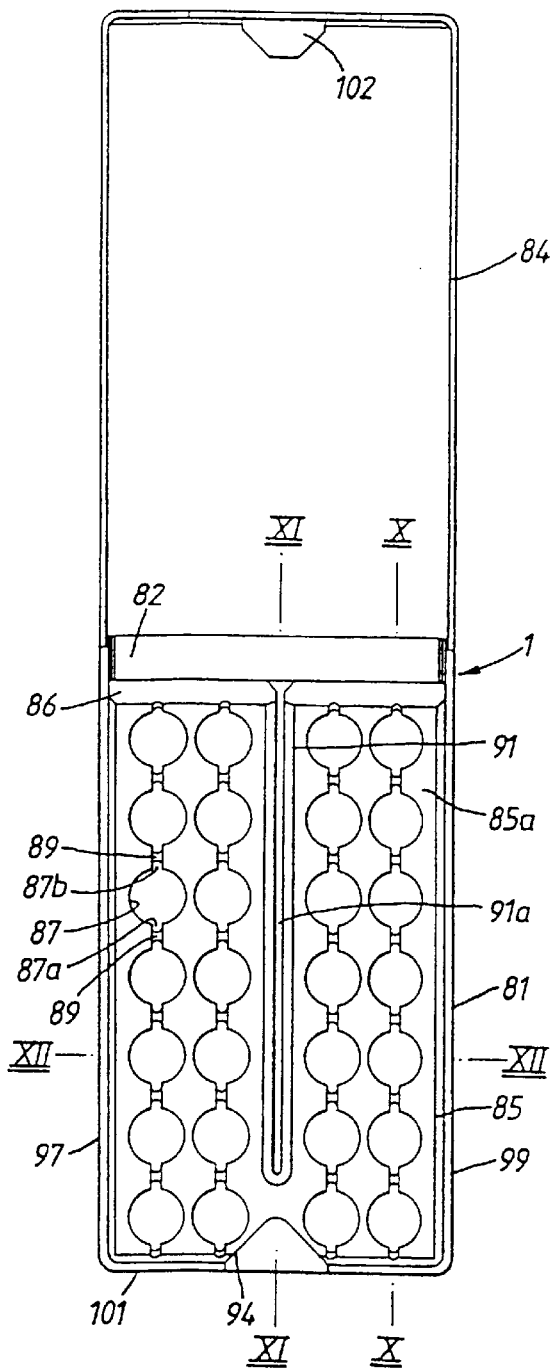
FIG. 20(e) illustrates a plan view of the support unit of FIG. 20(a), illustrated in the open or operative configuration.
Figure 20F:
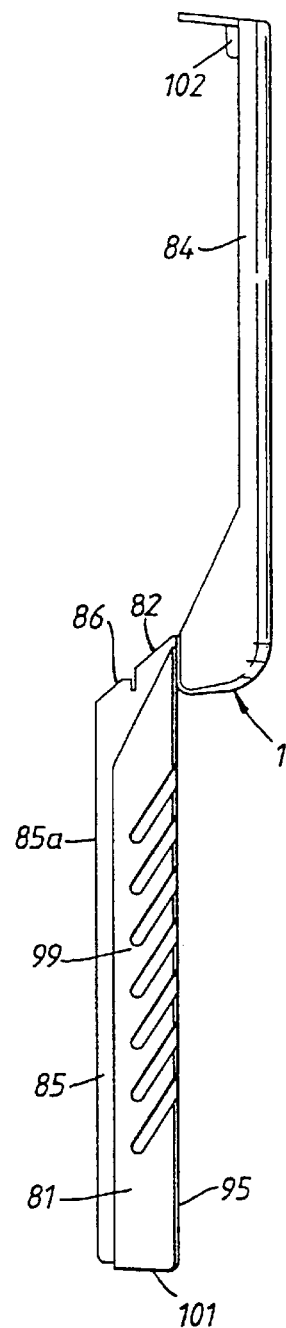
FIG. 20(f) illustrates a side view of the support unit of FIG. 20(a), illustrated in the open or operative configuration.
Figure 20I:
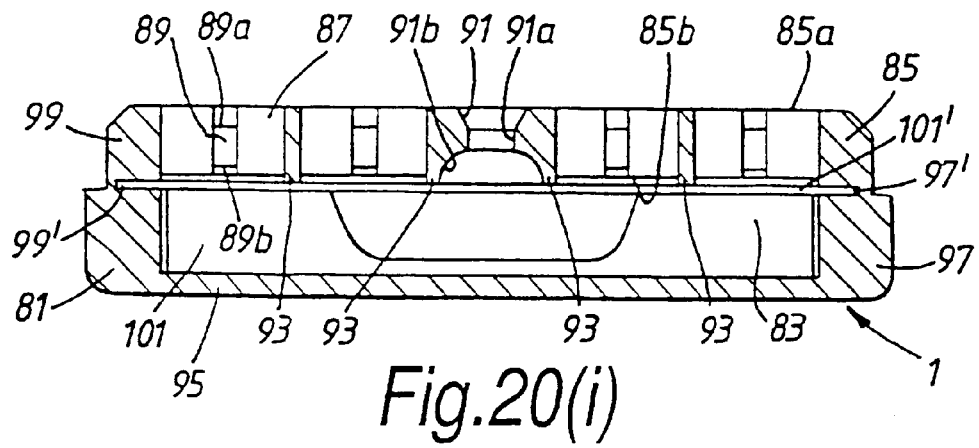
FIG. 20(i) illustrates in enlarged scale a vertical sectional view (along section XII—XII in FIG. 20(e)) of the support unit of FIG. 20(a), illustrated in the open or operative configuration.
Figure 31:
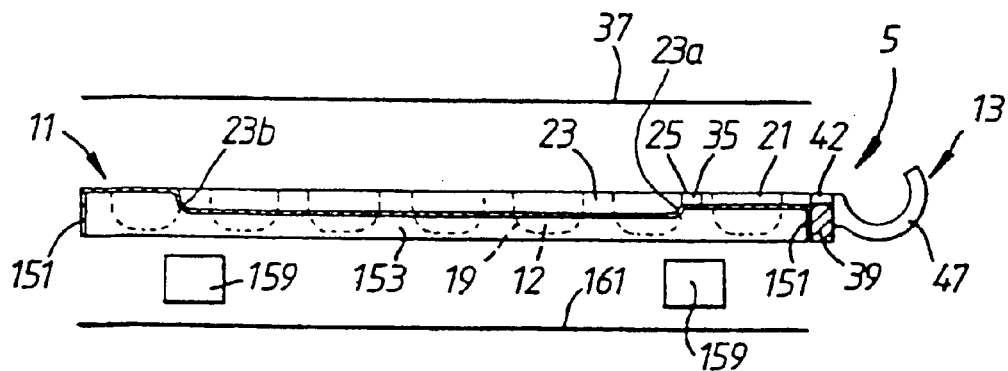
FIG. 31 illustrates an exploded vertical sectional view (along section XXIV—XXIV in FIG. 28) of the blister pack unit of the blister pack assembly of FIG. 28.

The inhaler comprises a support unit 1 and a blister pack assembly 3 which in use is loaded thereinto.

The blister pack assembly 3 comprises a blister pack unit 5, a suction tube 7 and an interconnecting member 9 which connects the suction tube 7 to the blister pack unit 5 so as to prevent the suction tube 7 from being inadvertently separated from the blister pack unit 5.

The blister pack unit 5 comprises a blister pack element 11, in this embodiment of generally rectaingular shape, which includes a plurality of blisters 12, each containing a dose of powder containing medicament, and an attachment member 13, to which the suction tube 7 is attachable, fixed to the blister pack element 11.

The blister pack element 11 comprises a substantially planar thin sheet 17 which includes a plurality of cavities 19, each defining a part of a respective blister 12, and first and second open channels 21, 23 which are separated by a web member 25 and extend along the longitudinal axis of the blister pack element 11. In this embodiment the sheet 17 is formed of a metal, such as aluminium, and the cavities 19 have a depth of about 4 mm and a diameter at the opening thereof of about 7.5 mm. In alternative embodiments the sheet 17 can be formed of a plastics material or a laminate of metal and plastics material. The first channel 21, in this embodiment a flattened U-shaped section, comprises first and second opposed side wall members 21a, 21b and a bottom wall member 21c. The first channel 21 is of relatively short length and extends to one narrow end 22 of the blister pack element 11 so as to allow for a sliding fit thereto of mutually configured parts of the attachment member 13 as will be described in more detail hereinbelow. The bottom wall member 21c of the first channel 21 includes a downwardly-directed projection 29 which acts as a detent for fixing the attachment member 13 in position relative to the blister pack element 11 as again will be described in more detail hereinbelow. The second channel 23, in this embodiment of arcuate section, is elongate and includes first and second end wall members 23a, 23b. The web member 25 separating the first and second channels 21, 23 includes a groove 35 which extends across the width thereof and along the longitudinal axis of the blister pack element 11.

The blister pack element 11 further comprises a thin film 37, in this embodiment in two sections, which is attached to the substantially planar surface of the sheet 17 thereof so as to cover the openings of each of the cavities 19 and thereby enclose a dose of powder containing medicament in each blister 12. In this embodiment the film 37 is formed of a metal, such as aluminium, and is attached to the sheet 17 by one of welding or an adhesive.

The attachment member 13 comprises an elongate body 39 which is of substantially the same length as the one narrow end 22 of the blister pack element 11, first and second projections 41, 43 which extend from the midpoint of one side surface of the elongate body 39 and together define a U-shaped channel 45 for receiving the first channel 21 in the sheet 17 of the blister pack element 11 and first and second clips 47, 49 which extend from the respective ends of the other side surface of the elongate body 39 and are each separately configured to hold the suction tube 7 when not in use. In this embodiment the clips 47, 49 are configured such that when the suction tube 7 is attached to one of the clips 47, 49 the other of the clips 47, 49 acts as a guard to protect against damage of the suction tube 7. The first projection 41, in this embodiment of rectangular section, is of the same section as the upper, inner surface of the first channel 21 in the sheet 17 of the blister pack element 11 so as to be a close slideable fit therein and includes a groove 42 which extends along the upper surface of the length thereof. The second projection 43, in this embodiment a flattened U-shaped section, comprises first and second opposed side wall members 43a, 43b and a bottom wall member 43c, with the first and second projections 41, 43 being configured such that the first and second side wall members 43a, 43b and the bottom wall member 43c of the second projection 43 are disposed opposite the side and bottom surfaces of the first projection 41. The upper, inner surface of the second projection 43 is of the same section as the outer, lower surface of the first channel 21 in the sheet 17 of the blister pack element 11 so as to be a close slideable fit thereabout, with the side wall members 43a, 43b of the second projection 43 being dimensioned so as to abut a lower surface of the sheet 17 of the blister pack element 11. The bottom wall member 43c of the second projection 43 includes an opening 51 therein for receiving the downwardly-directed projection 29 on the bottom wall member 21c of the first channel 21 in the sheet 17 of the blister pack element 11 when the attachment member 13 is fitted to the blister pack element 11 so as to fix the attachment member 13 in position relative to the blister pack element 11.

The suction tube 7, which will be described in further detail hereinbelow, comprises a generally elongate body 62 which includes an inlet section 63 at one end, which inlet section 63 includes a cutting assembly 64 for cutting the film 37 covering the cavities 19 of the blisters 12 in the blister pack element 11 and an inlet 65 through which powder containing medicament is in use drawn from a respective blister 12 on inhalation by a user. an outlet section 67 at the other end, which outlet section 67 includes an outlet 69 and provides a mouthpiece, and an inhalation channel 71 providing fluid communication between the inlet 65 and the outlet 69. The body 62 of the suction tube 7 includes at the outer surface thereof a plurality of ribs 73 for allowing a user to grip the same securely and a peripheral recess 75 for receiving a part of the interconnecting member 9 as will be described in more detail hereinbelow.

The interconnecting member 9 comprises a line 76 of a flexible material, preferably a plastics material, such as nylon, a clip 77 fixed to one end of the line 76 which is located in the peripheral recess 75 in the outer surface of the body 62 of suction tube 7 so as to anchor the line 76 to the same and an element 79 fixed to the other end of the line 76 which is of larger dimension than the gauge of the line 76 and is in use located partly in the second channel 21 in the sheet 17 of the blister pack element 11. In this embodiment the clip 77 is part-circular and formed of a resilient material so as to be a snap-fit about the body 62 of the suction tube 7. With this configuration, the line 76 is anchored to the suction tube 7 but yet allows the suction tube 7 to rotate relative thereto. As will become apparent hereinbelow, the suction tube 7, in being rotatable relative to the clip 77 of the interconnecting member 9, has a much greater freedom of movement and thereby facilitates use.

The support unit 1 comprises a housing 81 which includes an opening 82 and defines a cavity 83 into which the blister pack element 11 of the blister pack assembly 3 is in use inserted and a cover member 84 for enclosing the blister pack assembly 3 when not in use.

The housing 81 comprises a first, upper wall member 85 which, in this embodiment, is substantially planar and of rectangular shape. The upper wall member 85 includes an upper, outer surface 85*a* and a lower, inner surface 85*b* adjacent which the blister pack element 11 of the blister pack assembly 3 is in use disposed The upper wall member 85 also includes one free end 86 which defines a part of the opening 82 in the housing 81 through which the blister pack element 11 is in use inserted. The upper wall member 85 further includes a plurality of openings 87 which each overlie a respective one of the openings of the cavities 19 of the blisters 12 in the blister pack element 11 such that each of the blisters 12 can be emptied by inserting the suction tube 7 into a respective one of the openings 87. In this embodiment the openings 87 in the upper wall member 85 are each configured to have the same peripheral shape as the inlet section 63 of the suction tube 7 such that the openings 87 act as guides for guiding the inlet section 63 of the suction tube 7 into a respective blister 12 in the blister pack element 11. Each of the openings 87 includes first and second radial extensions 87*a*, 87*b* for receiving mutually configured parts on the inlet section 63 of the suction tube 7 as will be described hereinbelow. The radial extensions 87*a*, 87*b* of the openings 87 each include a web member 89 which includes upper and lower surfaces 89*a*, 89*b* that are substantially parallel respectively to the upper and lower surfaces 85*a*, 85*b* of the upper wall member 85 of the housing 81. The web members 89 are of lesser thickness than the upper wall member 85 of the housing 81 and are disposed such that the upper and lower surfaces 89*a*, 89*b* thereof are stepped back respectively from the upper and lower surfaces 85*a*, 85*b* of the upper wall member 85. The upper wall member 85 of the housing 81 further includes an elongate slot 91 which extends from the one free end 86 thereof, in this embodiment along the longitudinal axis of the housing 81, and overlies the second channel 23 in the sheet 17 of the blister pack element 11 when fitted such that the line 76 of the interconnecting member 9 can be drawn thereinto and pass freely therealong. The elongate slot 91 includes a first, narrow section 91*a* at the upper surface 85*a* of the upper wall member 85 which is of a width smaller than the smallest dimension of the element 79 of the interconnecting member 9 so as to prevent that element 79 from passing therethrough and a second, wide section 91*b* at the lower surface 85*b* of the upper wall member 85 for receiving a part of the element 79 of the interconnecting member 9. In this embodiment the wide section 91*b* of the elongate slot 91 is arcuate in shape and flares outwardly to the lower surface 85*b* of the upper wall member 85. The upper wall member 85 of the housing 81 still further includes a plurality of elongate ribs 93 which extend downwardly from the lower surface 85*b* thereof parallel to the longitudinal axis of the housing 81. The ribs 93 are provided to space the upper surface of the blister pack element 11 from the lower surface 85*a* of the upper wall member 85 and thereby provide an air flow path to the blisters 12 in the blister pack element 11. Further, in this embodiment, one rib 93 is located on either side of the elongate slot 91 in the upper wall member 85 such that when the blister pack assembly 3 is fitted to the support unit 1 the second channel 23 in the sheet 17 of the blister pack element 11 and the wide section 91*b* of the elongate slot 91 define an enclosed track in which the element 79 of the interconnecting member 9 is captively held, with the limits of movement of the element 79 along the enclosed track being defined by the end wall members 23*a*, 23*b* of the second channel 23 in the sheet 17 of the blister pack element 11. It will be appreciated that this configuration, in not having the line 76 of the interconnecting member 9 fixed at one point, is advantageous in that the line 76 of the interconnecting member 9 need only be as long as the distance between the furthest most opening 87 and the elongate slot 91 in the upper wall member 85, which distance, in this embodiment, corresponds to approximately half of the width of the upper wall member 85. The upper wall member 85 of the housing 81 still further includes a recess 94 at that end thereof remote from the opening 82 in the housing 81. This recess 94 provides a means by which a user can push the blister pack element 11 a distance out of the housing 81 so as to facilitate withdrawal of the blister pack assembly 3.

The housing 81 further comprises a second, lower wall member 95, in this embodiment substantially planar and of rectangular shape, which is spaced in parallel relation to the upper wall member 85, first and second side wall members 97, 99 which extend between the sides of the upper and lower wall members 85, 95 and an end wall member 101 which extends between the ends of the upper and lower wall members 85, 95 remote from the opening 82 in the housing 81. In this embodiment the side wall members 97, 99 and the end wall member 101 each include a groove 97', 99', 101' into which the peripheral edge at the sides and the other end of the blister pack element 11 of the blister pack assembly 3 is in use located such that the blister pack element 11 is held in position adjacent the lower surface 85*b* of the upper wall member 85 of the housing 81.

The cover member 84 is hinged to the housing 81, in this embodiment at that end adjacent the opening 82 therein. In a preferred embodiment the housing 81 and the cover member 84 of the support unit 1 are integrally formed of a plastics material such that the hinged connection of the housing 81 and the cover member 84 is provided by a living hinge. The cover member 84 includes a catch member 102 at the free end thereof which is configured to engage the recess 94 in the upper wall member 85 of the housing 81 when the cover member 84 is closed and thereby hold the same closed.

As described hereinabove, the suction tube 7 includes an inlet section 63 which includes a cutting assembly 64 for cutting the film 37 covering the cavities 19 of the blisters 12 in the blister pack element 11.

The inlet section 63 of the suction tube 7 further includes first and second arms 105, 107 which extend forwardly, in the sense of insertion of the suction tube 7 into a blister 12, from respective sides thereof and are biased outwardly. The arms 105, 107 are each configured so as to be a sliding fit in the radial extensions 87*a*, 87*b* of the openings 87 in the upper wall member 85 of the housing 81. In this way, the suction tube 7 can only be inserted into an opening 87 in the upper wall member 85 of the housing 81 in one of two orientations, and, as will become apparent hereinbelow, since the cutting assembly 64 has two-fold rotational symmetry, the suction tube 7 can never inadvertently be inserted into a blister 12 with another orientation which may cause the film 37 covering the respective blister 12 to be cut free. It will, of course, be appreciated that in any embodiment where the cutting assembly 64 of the suction tube 7 does not have such rotational symmetry the first and second arms 105, 107 at the inlet section 63 of the suction tube 7 and the radial extensions 87a, 87b of the openings 87 hi the upper wall member 85 of the housing 81 can be configured so as to permit the suction tube 7 to be inserted into the openings 87 in the upper wall member 85 of the housing 81 in only one orientation. Each of the first and second arms 105, 107 includes a catch member 109, 14 which is adapted to engage with the web members 89 in the radial extensions 87a, 87b of the openings 87 in the upper wall member 85 of the housing. 81. The catch members 109, 111 on the first and second arms 105, 107 each have a first surface 109a, 111 which has a forwardly-directed component and acts as a guiding surface and a second surface 109b. 111b which is substantially orthogonally directed to the longitudinal axis of the body 62 of the suction tube 7 and acts as a locking surface. In use, on fitting the suction tube 7 to the housing 81, the second, locking surfaces 109b, 111b of the catch members 109, 111 snap behind respective ones of the lower surfaces 89b of the web members 89 in the radial extensions 87a, 87b of the openings 87 in the upper wall member 85 of the housing 81 so as to prevent the suction tube 7 from falling out of the respective opening 87 and thereby avoid the need for the user continuously to hold the suction tube 7 in position. It will be appreciated that the catch members 109, 111, in being a snap fit, provide the user with a clear indication that the suction tube 7 is correctly fitted to the housing 81 and hence inserted into a respective one to of the blisters 12 in the blister pack element 11. In this regard, the second, locking surfaces 109b, 111b of the catch members 109, 111 are configured so as to have only a small radial extent such as to allow the suction tube 7 to be removed from a respective one of the openings 87 in the upper wall member 85 of the housing 81 after use on the application of a light force.

The inlet section 63 of the suction tube 7 yet further includes a plurality of lugs 115 which extend radially therefrom and each include a lower surface 115' which defines a first shoulder that acts to limit the extent to which the suction tube 7 can be inserted into any of the openings 87 in the upper wall member 85 of the housing 81 and hence a respective blister 12 in the blister pack element 11. In this embodiment the lugs 115 are configured such that the shoulder defined by the lower surfaces 115' thereof abuts the upper surface 85a of the upper wall member 85 of the housing 81 on the required insertion of the suction tube 7 into one of the openings 87 in the upper wall member 85 of the housing 81. In this way, the suction tube 7 cannot be inserted too far into a blister 12 which could result in the cutting assembly 64 at the inlet section 63 of the suction tube 7 being forced inadvertently through the cavity 19 of any blister 12 on fitting the suction tube 7 to the housing 81.

The inlet section 63 of the suction tube 7 still further includes first and second axially-extending members 117, 119 which each include a lower surface 117', 119' that defines a second shoulder which is racially forward, in the sense of inserting the suction tube 7 into one of the openings 87 in the upper wall member 85 of the housing 81, of the first shoulder defined by the lower surfaces 115' of the lugs 115. In this embodiment the first and second axially-extending members 117, 119 are configured such that the second shoulder defined by the lower surfaces 117', 119' thereof abuts the upper surface of the blister pack element 11 when the first shoulder defined by the lower surfaces 115' of the lugs 115 abuts the upper surface 85a of the upper wall member 85 of the housing 81.

The cutting assembly 64 of the inlet section 63 of the suction tube 7 comprises a cutting blade 127 and first and second ram blades 129, 131 disposed adjacent thereto.

The cutting blade 127 includes a cutting edge 133 which extends across and is located axially forward, in the sense of inserting the suction tube 7 into one of the openings 87 in the upper wall member 85 of the housing 81, of the inlet 65 of the suction tube 7 such that, on insertion of the suction tube 7 into one of the openings 87 in the upper wall member 85 of the housing 81, a cut is made in the film 37 covering the opening of the cavity 19 of the blister 12 therebeneath. In this embodiment the cutting edge 133 of the cutting blade 127 includes a cutting point 133'. The cutting blade 127, which in this embodiment is substantially planar, is co-axial with the longitudinal axis of the body 62 of the suction tube 7 and includes first and second flank sections 127a, 127b which taper to an axially-foremost cutting point 127c located on the longitudinal axis of the body 62 of the suction tube 7. In this embodiment the flank sections 127a, 127b of the cutting blade 127 enclose an angle of about 120 degrees. The cutting blade 127 has an effective cutting length approaching that of the diameter of the openings to the cavities 19 of the blisters 12 in the blister pack element 11 such that, on insertion of the suction tube 7 into a respective one of the openings 87 in the upper wall member 85 of the housing 81, the cutting blade 127 cuts the film 37 across the diameter of the opening to the cavity 19 of the respective blister 12. The cutting blade 127 further includes a transverse opening 134 located behind the cutting edge 133 thereof for providing an air flow path therethrough.

The first and second ram blades 129, 131, which in this embodiment are each substantially planar. are located to each side of the cutting blade 127, and, as will be described in more detail hereinbelow, are configured to bear on and push back the film 37 covering the cavity 19 of a respective one of the blisters 12 once cut by the cutting blade 127 and thereby open the blister 12. In this embodiment the first and second ram blades 129, 131 are disposed parallel to, and are the same radial distance from, the cutting blade 127. The first and second ram blades 129, 131 each include a lower, axially-forward surface 129', 131' which is located axially rearward of the axially foremost part of the cutting edge 133 of the cutting blade 127 such that the ram blades 129, 131 act on the film 37 only once at least partly cut by the cutting blade 127. In this embodiment the bearing surface 129', 131' of each of the ram blades 129, 131 is substantially flat In a preferred embodiment the cutting assembly 64 of the suction tube 7 is configured such that the effective length of each of the bearing surfaces 129', 131' of the ram blades 129, 131, that is, the distance between the endmost points of the bearing surface 129', 131' of each of the ram blades 129, 131, is approximately the same distance as the distance between. the adjacent endmost points of the bearing surfaces 129', 131' of the ram blades 129, 131 and the endmost points of the effective cutting length of the cutting blade 127. In this way, the film 37 covering the openings of the cavities 19 of any of the blisters 12 in the blister pack element 11 will be broken into flaps 136a–f of substantially equal size.

Figure 21A:
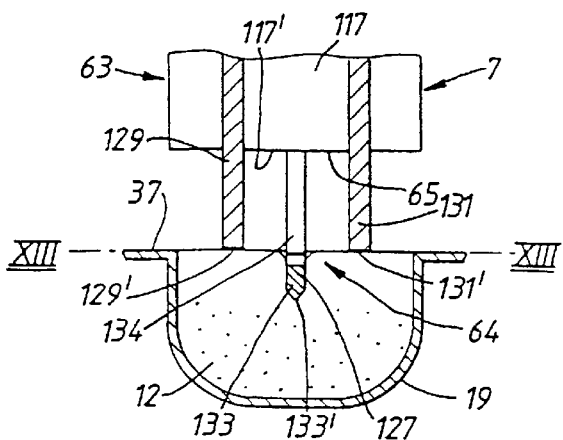
FIG. 21(a) illustrates a fragmentary vertical sectional view (along section IX—IX in FIG. 18(b)) of the suction tube of FIG. 18(a) when partly inserted into a blister.
Figure 21B:
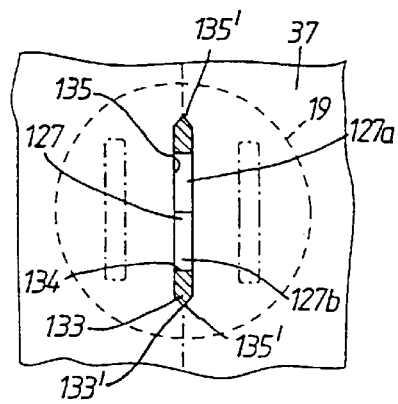
FIG. 21 (b) illustrates a horizontal sectional view (along section XIII—XIII in FIG. 21(a)) of the suction tube of FIG. 18(a) when partly inserted into a blister.
Figure 22A:
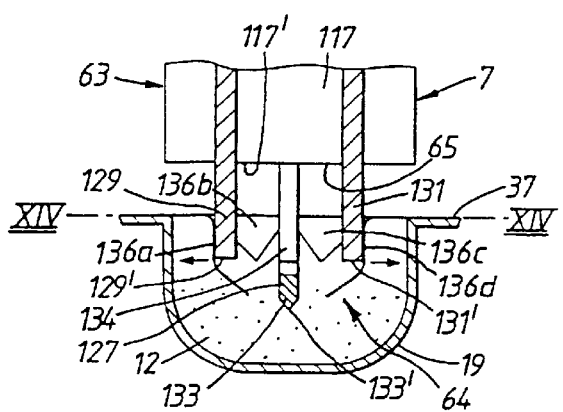
FIG. 22(a) illustrates a fragmentary vertical sectional view (along section IX—IX in FIG. 18(b)) of the suction tube of FIG. 18(a) when further inserted into a blister.
Figure 22B:
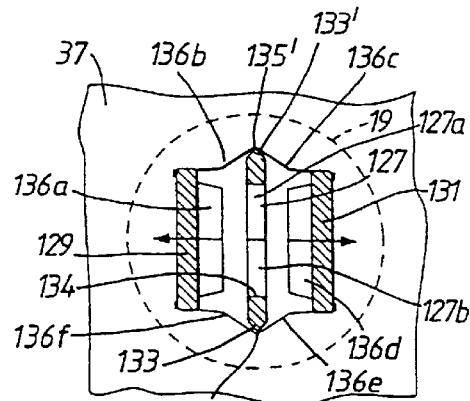
FIG. 22(b) illustrates a horizontal sectional view (along section XIV—XIV in FIG. 22(a)) of the suction tube of FIG. 18(a) when further inserted into a blister.
Figure 23A:
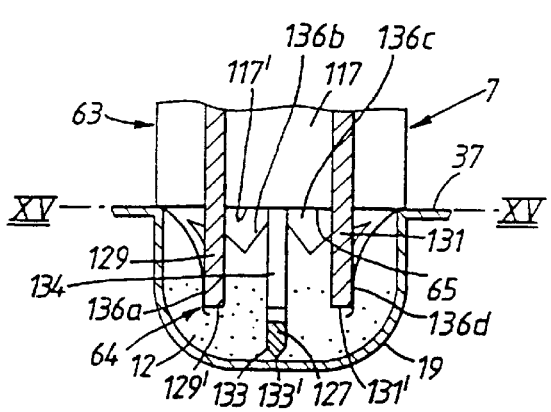
FIG. 23(a) illustrates a fragmentary vertical sectional view (along section IX—IX in FIG. 18(b)) of the suction tube of FIG. 18(a) when fully inserted into a blister.
Figure 23B:
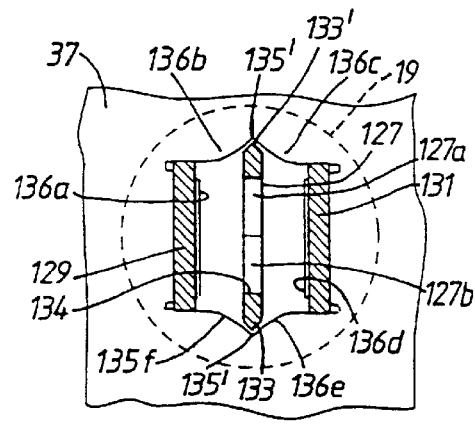
FIG. 23(b) illustrates a horizontal sectional view (along section XV—XV in FIG. 23(a)) of the suction tube of FIG. 18(a) when fully inserted into a blister.

The action of the cutting assembly 64 of the suction tube 7 is clearly illustrated in FIGS. 21 to 23. In a first step, as illustrated in FIGS. 21(a) and 21(b), as the cutting assembly 64 is inserted into a blister 12 the cutting blade 127 makes a cut 135 across the diameter of the. as; film 37 covering the opening of the cavity 19 of the blister 12. In a second step, as illustrated in FIGS. 22(a) and 22(b), as the cutting assembly 64 is inserted further into the blister 12 the bearing surfaces 129', 131' of the ram blades 129, 131 act on the film 37 and cause the film 37 to tear between adjacent endmost points of the bearing surface 129', 131' of the ram blades 129, 131 and the ends 135; of the cut 135 so as to form six flaps 136a–f. As mentioned hereinabove, in a preferred embodiment the cutting blade 127 and the ram blades 129, 131 are configured such that the flaps 136a–f are of substantially equal size. In a final step, as illustrated in FIGS. 23(a) and 23(b), the cutting assembly 64 is inserted further into the blister 12 until the second shoulder defined by the lower surfaces 117', 119' of the axially-directed members 117, 119 is at the upper surface of the blister pack element 11. In this position the suction tube 7 is inserted fully into the blister 12. In inserting the cutting assembly 64 further into blister 12 the ram blades 129, 131 cause the flaps 136a–f to be pushed to the wall of the cavity 19 of the blister 12 so as to provide a large opening in the film 37 covering the blister 12 which allows for the ready withdrawal of powder therefrom.

The inlet section 63 of the suction tube 7 still yet further includes first and second upper supplementary air inlet openings 137, 139 into the inhalation channel 71 of the suction tube 7. The first and second upper supplementary air inlet openings 137, 139 into the inhalation channel 71 provide supplementary air flow paths, which, on inhalation by a user, allow supplementary air to be drawn into the inhalation channel 71 and mix with the air and powder mixture drawn through the inhalation channel 71 from a blister 12 in the blister pack element 11. As will be appreciated, the provision of such supplementary air flow paths provides that for each unit volume of air inhaled the user inhales a reduced amount of powder containing medicament. Furthermore, the action of supplementary air mixing with an air and powder mixture drawn through the inhalation channel 71 induces turbulence and assists in the deagglomeration of that powder.

FIGS. 24 to 27 illustrate modified suction tubes 7 for the inhaler described hereinabove. Structurally, these modified suction tubes 7 are similar to the suction tube 7 of the inhaler described hereinabove and differ only in aspects of the inlet section 63, principally the cutting assembly 64. For this reason, and in order to avoid unnecessary duplication of description, only the structural differences of the suction tubes 7 will be described in detail and reference is made to the preceding description.

Figure 24A:
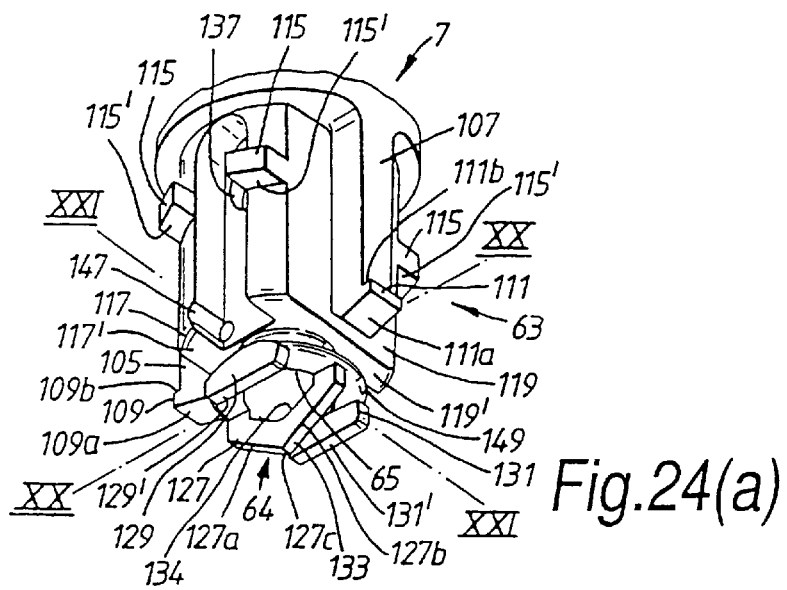
FIG. 24(a) illustrates a fragmentary perspective view of a first modified suction tube for the inhaler of FIG. 1.
Figure 24B:
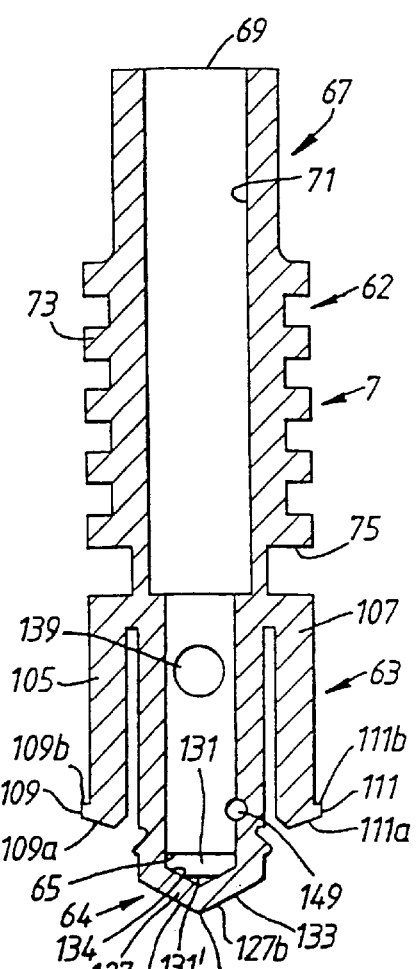
FIG. 24(b) illustrates a vertical sectional view (along section XVI—XVI in FIG. 24(a)) of the suction tube of FIG. 24(a)
Figure 24C:
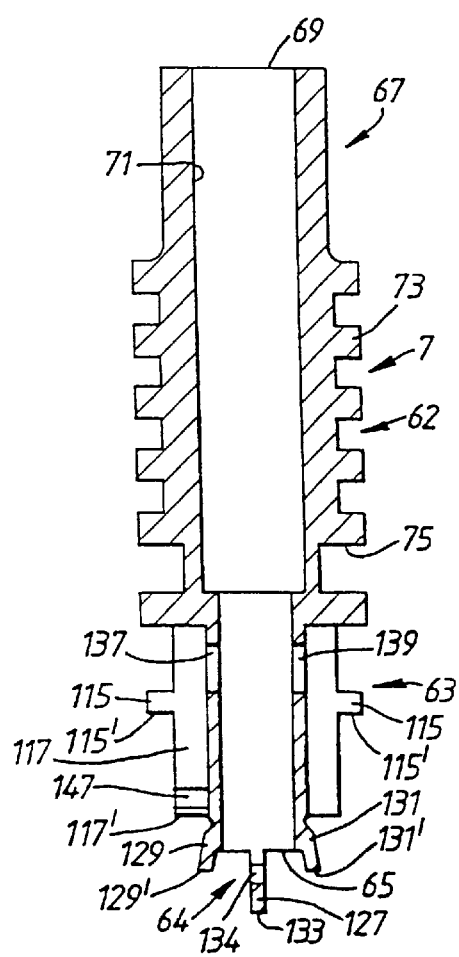
FIG. 24(c) illustrates a vertical sectional view (along section XVII—XVII in FIG. 24(a)) of the suction tube of FIG. 24(a)

FIGS. 24(a) to (c) illustrate a first modified suction tube 7. This suction tube 7 differs from the first-mentioned suction tube 7 in two aspects. Firstly, the ram blades 129, 131 each include an opening 141, 143 which extends axially rearwardly from the bearing surface 129', 131' thereof for providing shorter air flow paths between the periphery of the cavity 19 of the blister 12 adjacent the rain blades 129, 131 and the inlet 65. Secondly, the inlet 65 to the inhalation channel 71 is located axially forward, in the sense of insertion of the suction tube 7 into a blister 12, of the second shoulder defined by the lower surfaces 117', 119' of the axially-extending members 117, 119 which in use is located at the upper surface of the blister pack element 11. With this configuration, the inlet 65 to the inhalation channel 71 is located within each blister 12 and thereby forces air to be drawn more deeply into the cavity 19 of the blister 12 on inhalation by a user.

Figure 25A:
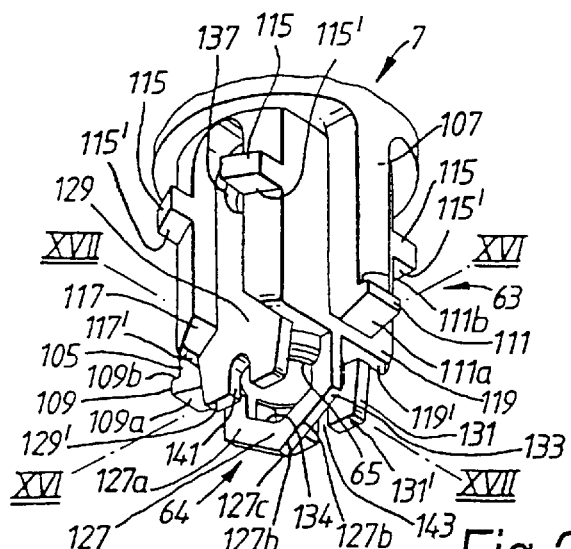
FIG. 25(a) illustrates a fragmentary perspective view of a second modified suction tube for the inhaler of FIG. 1.
Figure 25B:
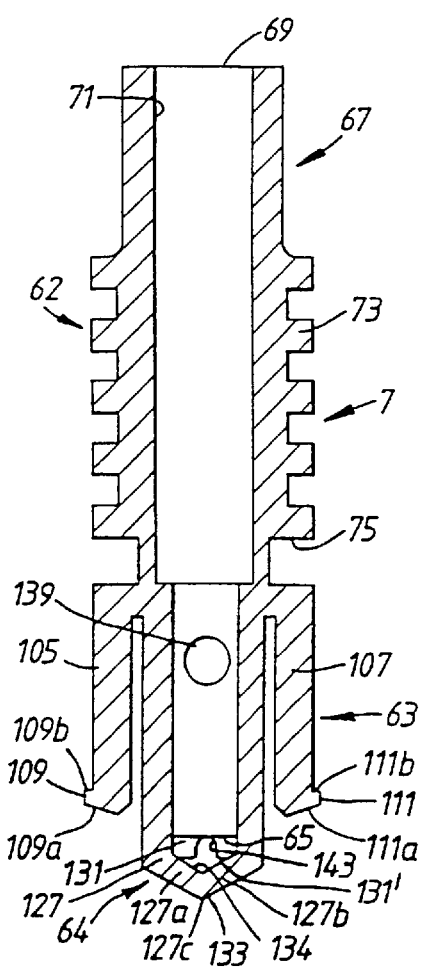
FIG. 25(b) illustrates a vertical sectional view (along section XVIII—XVIII in FIG. 25(a)) of the suction tube of FIG. 25(a)
Figure 25C:
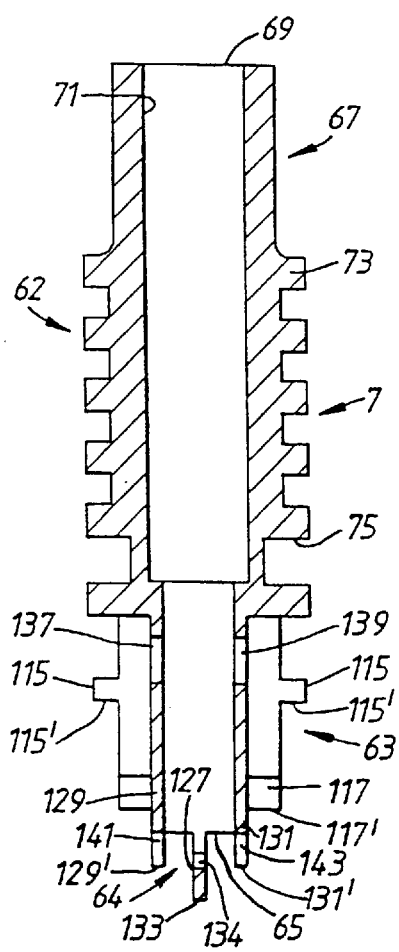
FIG. 25(c) illustrates a vertical sectional view (along section XIX—XIX in FIG. 25(a)) of the suction tube of FIG. 25(a)

FIGS. 25(a) to (c) illustrate a second modified suction tube 7, This suction tube 7 differs from the first-modified suction tube 7 in that the transverse opening 141, 143 in each of the ram blades 129, 131 is within the respective ram blade 129, 131.

FIGS. 26(a) to (c) illustrate a third modified suction tube 7. This suction tube 7 differs from the first-mentioned suction tube 7 in two aspects. Firstly, the inlet section 63 of the suction tube 7 further includes first and second lower supplementary air inlet openings 147, 149 into the inhalation channel 71 at a position adjacent, but in this embodiment axially rearward, in the sense of insertion of the suction tube 7 into a blister 12, of the second shoulder defined by the lower surfaces 117', 119' of the axially-extending members 117, 119 which in use is located at the upper surface of the blister pack element 11. These first and second lower supplementary air inlet openings 147, 149 provide a supplementary air flow path into the inhalation channel 71 which promotes turbulent flow within the cavity 19 of the blister 12, which turbulence, as will be appreciated, assists in emptying the blister 12. Secondly, the inlet 65 to the inhalation channel 71 is located axially forward, in the sense of insertion of the suction tube 7 into a blister 12, of the second shoulder defined by the lower surfaces 117', 119' of the axially extending members 117, 119 which in use is located at the upper surface of the blister pack element 11. A described hereinabove in relation to the first-modified suction tube 7, with this configuration the inlet 65 to the inhalation channel 71 is located within each blister 12 and thereby forces air to be drawn more deeply into the cavity 19 of the blister 12 on inhalation by a user.

Figure 27A:
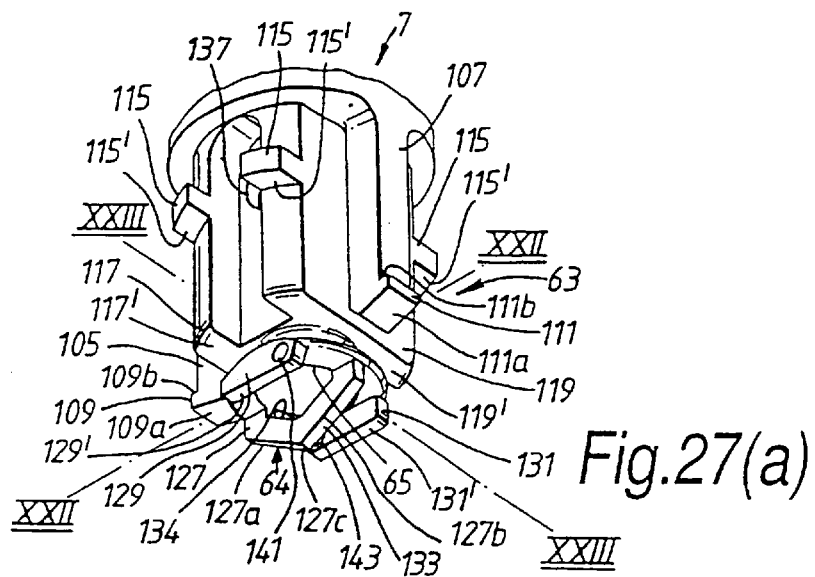
FIG. 27(a) illustrates a fragmentary perspective view of a fourth modified suction tube for the inhaler of FIG. 1.
Figure 27B:
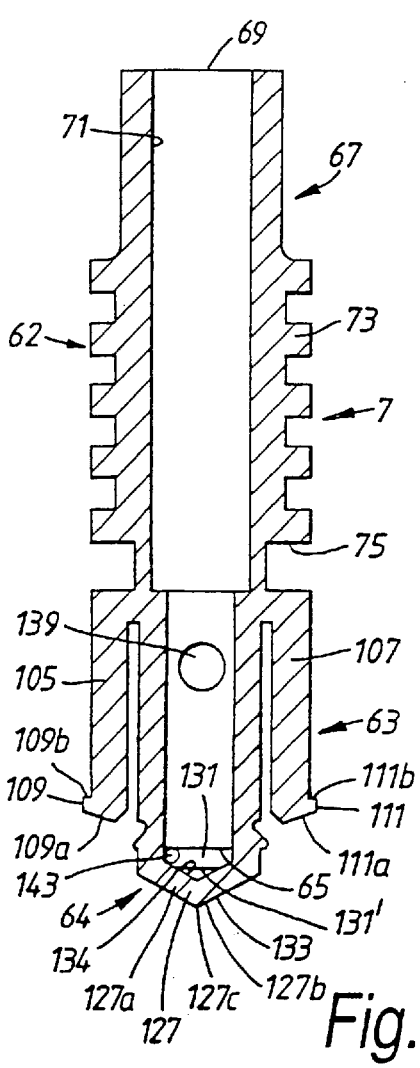
FIG. 27(b) illustrates a vertical sectional view (along section XXII—XXII in FIG. 27(a)) of the suction tube of FIG. 27(a)
Figure 27C:
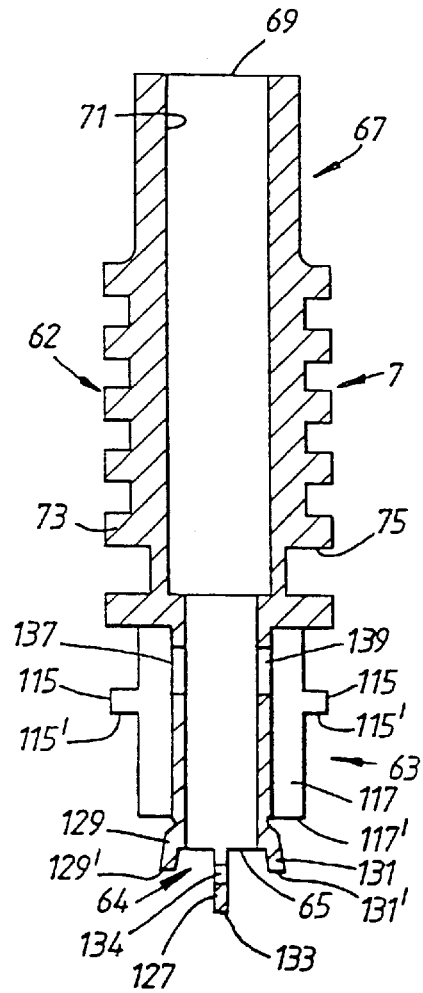
FIG. 27(c) illustrates a vertical sectional view (along section XXIII—XXIII FIG. 27(a)) of the suction tube of FIG. 27(a)
Figure 28:
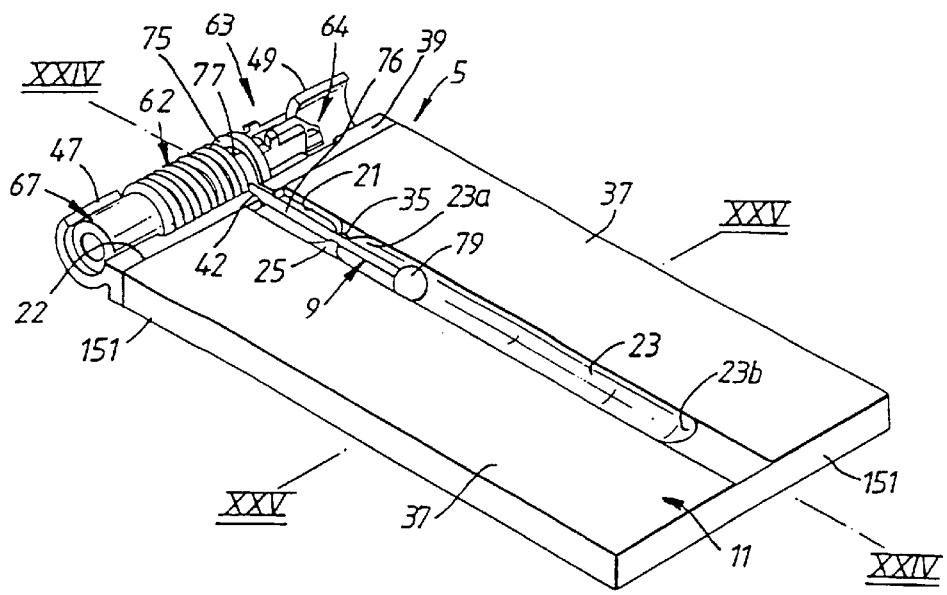
FIG. 28 illustrates a perspective view of a modified blister pack assembly for the inhaler of FIG. 1.
Figure 29:
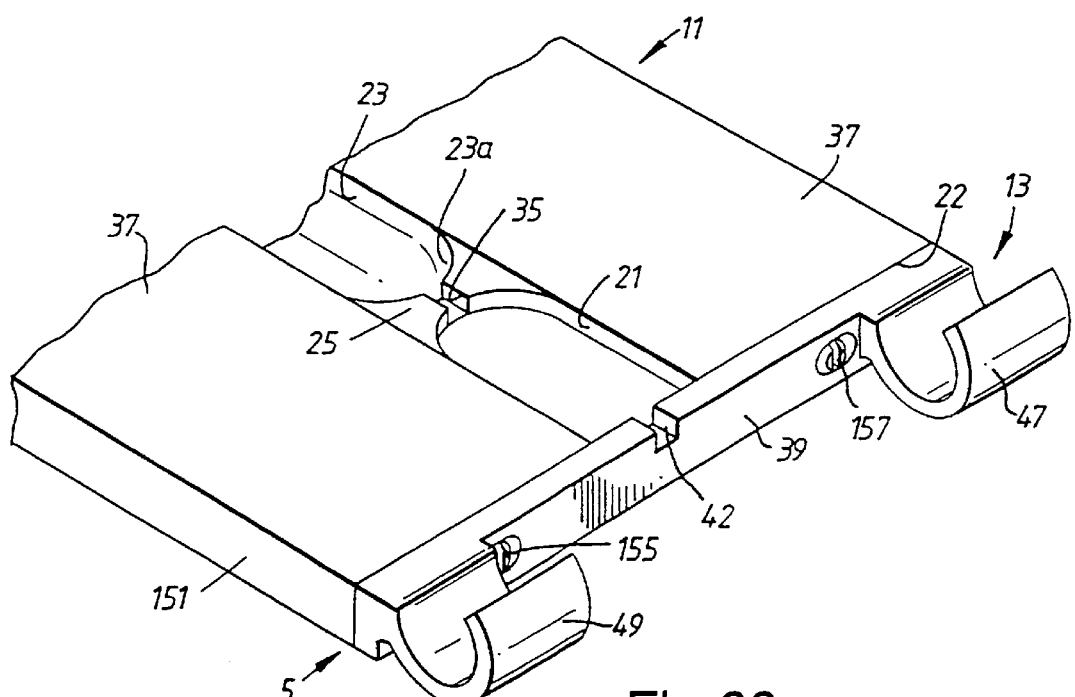
FIG. 29 illustrates in enlarged scale a frgentary perspective view of the blister pack unit of the blister pack assembly of FIG. 28.
Figure 30:
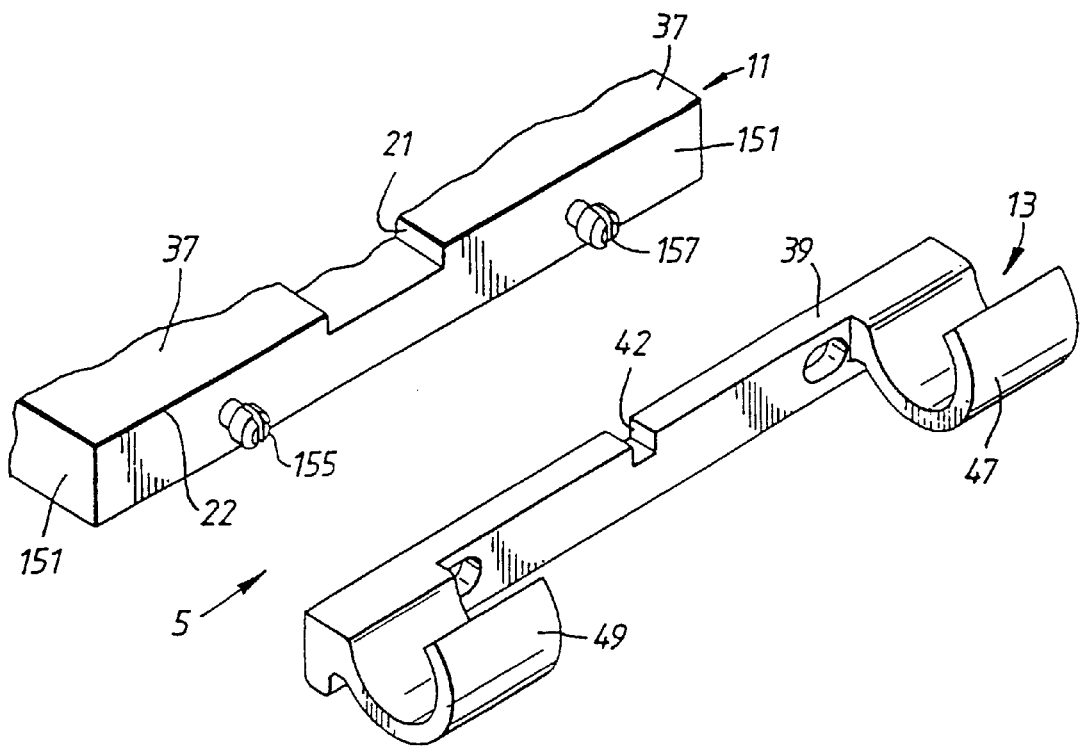
FIG. 30 illustrates in enlarged scale a fragmentary exploded perspective view of the blister pack unit of the blister pack assembly of FIG. 28.
Figure 32:
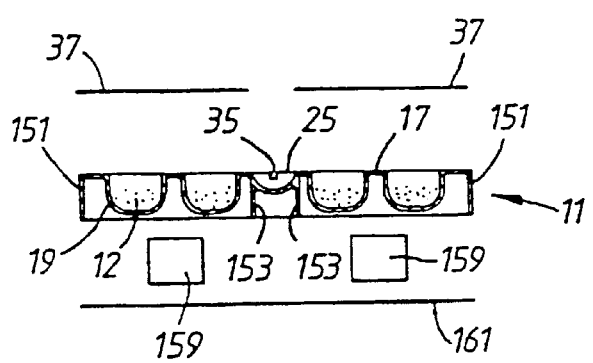
FIG. 32 illustrates an exploded vertical sectional view (along section XXV—XXV in FIG. 28) of the blister pack unit of the blister pack assembly of FIG. 28.

FIGS. 27(a) to (c) illustrate a fourth modified suction tube 7. This suction tube 7 differs from the first-mentioned suction tube 7 in two aspects. Firstly, the ram blades 129, 131 each include a transverse opening 141, 143 for providing shorter air flow paths between the periphery of the cavity 19 of the blister 12 adjacent the ram blades 129, 131 and the inlet 65. In this embodiment the openings 141, 143 in the ram blades 129, 131 are asymmetrically located so as to promote turbulent flow in the cavities 19 of the blisters 12. Secondly, the inlet 65 to the inhalation channel 71 is located axially forward, in the sense of insertion of the suction tube 7 into a blister 12, of the second shoulder defined by the lower surfaces 117', 119' of the axially-extending members 117, 119 which in use is located at the upper surface of the blister pack element 11. As again described hereinabove in relation to the fist-modified suction tube 7, with this configuration the inlet 65 to the inhalation channel 71 is located within each blister 12 and thereby forces air to be drawn more deeply into the cavity 19 of the blister 12 on inhalation by a user.

FIGS. 28 to 32 illustrate a modified blister pack assembly 3 for the inhaler described hereinabove. Structurally, this modified blister pack assembly 3 is similar to the blister pack assembly 3 of the inhaler described hereinabove and differs only in aspects of the blister pack unit 5. For this reason, and in order to avoid unnecessary duplication of description, only the structural differences of the blister pack assemblies 3 will be described in detail and reference is made to the preceding description. This modified blister pack unit 5 differs principally from the blister pack unit 5 of the blister pack assembly 3 of the inhaler described hereinabove in that the sheet 17 of the blister pack element 11 includes a downwardly depending peripheral skirt 151 and a plurality of downwardly-directed elongate ribs 153 which extend parallel to the longitudinal axis of the blister pack element 11. With this configuration the blister pack element 11 is configured to be a sliding fit in the cavity 83 of the housing 81 of the support unit 1, with the blister pack element 11 being self-supporting by the provision of the skirt 151 and the ribs 153. This modified blister pack unit 5 further differs from the blister pack unit 5 of the blister pack assembly 3 of the inhaler described hereinabove in the manner of the connection of the attachment member 13 in that the blister pack element 11 includes first and second projections 155, 157 at the. one end 22 thereof to which the attachment member 13, which is also modified in not including the first and second projections 41, 43, is snap fitted. This modified blister pack unit 5 yet further differs from the blister pack unit 5 of the blister pack assembly 3 of the inhaler described hereinabove in further including moisture permeable chambers 159 which contain desiccant disposed to the lower surface of the sheet 17 of the blister pack element 11 at at least some of the junctions between the cavities 19 defining the blisters 12 and in including a thin film 161 covering the lower surface thereof.

In use, a user takes the inhaler in one hand and opens up the cover member 84 of the support unit 1 so as to expose the suction tube 7 and the upper wall member 85 of the housing 81. The user then unclips the suction tube 7 from the attachment member 13 and inserts the inlet section 63 of the suction tube 7 through one of the openings 87 in the upper wall member 85 of the housing 81 and into an unused blister 12. In inserting the inlet. section 63 of the suction tube 7 into one of the openings 87 in the upper wall member 85 of the housing 81, the user has first to align the arms 105, 107 thereon with the radial extensions 87a, 87b of the openings 87 and then push in the suction tube 7 until the first shoulder defined by the lower surfaces 115' of the lugs 115 abuts the upper surface 85a of the upper wall member 85 and the catches 109, 111 on the arms 105, 107 snap behind the web members 89 in the radial extensions 87a, 87b of the openings 87. The user then takes the mouthpiece provided by the outlet section 67 of the suction tube 7 in his/her lips and inhales so as to withdraw the dose of powder containing powder from the blister 12 and deliver the same into the lungs. After inhalation, the user. withdraws the suction tube 7 from the opening 87 in the upper wall member 85 of the housing 81, which will require the application of a light force to overcome the action of the catches 109, 111 on the arms 105, 107 of the suction tube 7, and then clips the suction tube 7 back to the attachment member 13. This pattern of use can be repeated until all of the blisters 12 in the blister pack element 11 of the blister pack assembly 3 have been used. When all of the blisters 12 in the blister pack element 11 have been used, the user withdraws the blister pack assembly 3 form the support unit 1 and replaces that used blister pack assembly 3 with a new blister pack assembly 3.

Finally, it will be understood by a person skilled in the art that the present invention is not limited to the described embodiments but can be modified in many different ways without departing from the scope of the invention as defined by the appended claims.

What is claimed is:

1. An inhaler for administering powder containing medicament by inhalation, comprising:

a suction tube through which powder is in use drawn on inhalation by a user;

a support unit for supporting a blister pack element which includes a plurality of blisters, each containing a dose of powder containing medicament; and an interconnecting member connecting the suction tube to the support unit, wherein the interconnecting member includes an element which is slidably disposed to the support unit, wherein the interconnecting member is moveably coupled to the suction tube.

2. The inhaler according to claim 1, wherein the support unit includes an elongate slot in which the element of the interconnecting member is captively slidably disposed.

3. An inhaler according to claim 1, wherein the interconnecting member includes a clip to which the suction tube is moveably coupled.

4. The inhaler according to claim 1, wherein the suction tube comprises an elongate body which includes an inlet section at one end thereof, which inlet section includes an inlet and a cutting assembly comprising a cutting blade which includes a cutting edge for making a cut in the covering film of a blister and at least one ram blade which includes a bearing surface for bearing on the covering film of the blister and pushing the same into the cavity of the blister an outlet section at the other end thereof, which outlet section includes an outlet and provides a mouthpiece and an inhalation channel providing fluid communication between the inlet and the outlet through which powder is in use drawn on inhalation by a user.

5. The inhaler according to claim 1 further comprising a blister pack element which includes a plurality of blisters, each containing a dose of powder containing medicament.

6. The inhaler according to claim 5, wherein the blister pack element includes an elongate channel and the element of the interconnecting member in use is slidably disposed in the channel.

7. The inhaler according to claim 6, wherein the elongate channel extends along the longitudinal axis of the blister pack element.

8. The inhaler according to claim 5, wherein the blister pack element includes at least one moisture permeable chamber which contains a desiccant.

9. The inhaler according to claim 8, wherein the at least one moisture permeable chamber is disposed between cavities of the blisters.

10. The inhaler according to claim 5, wherein the support unit includes a wall member which includes a plurality of openings adjacent which the blister pack element is in use disposed such that a blister is located beneath each opening.

11. The inhaler according to claim 5, wherein the support unit includes an elongate slot which together with an elongate channel in the blister pack element defines an elongate track in which the element of the interconnecting member is captively slidably disposed.

12. The inhaler according to claim 11, wherein the elongate slot extends along the longitudinal axis of the support unit.

13. The inhaler according to claim 11, wherein the elongate slot includes a narrow section through which the element of the interconnecting member cannot pass.

14. The inhaler according to claim 11, wherein the elongate slot is located in the wall member of the support unit.

* * * * *